United States Patent [19]
Minato et al.

[11] Patent Number: 5,831,024
[45] Date of Patent: Nov. 3, 1998

[54] SPA-1 PROTEIN

[75] Inventors: Nagahiro Minato, Kyoto; Masakazu Hattori, Nagaokakyo; Hiroshi Kubota, Kyoto; Masatsugu Maeda, Tokorozawa, all of Japan

[73] Assignee: Nagahiro Minato, Kyoto, Japan

[21] Appl. No.: 380,403

[22] Filed: Jan. 30, 1995

Related U.S. Application Data

[63] Continuation-in-part of Ser. No. 325,909, Oct. 19, 1994, abandoned.

[30] Foreign Application Priority Data

May 30, 1994 [JP] Japan ................................ 6-139513

[51] Int. Cl.$^6$ .............................. C07K 14/00; C12N 9/22
[52] U.S. Cl. ........................... 530/358; 530/350; 435/199
[58] Field of Search .................................... 530/350, 351, 530/358; 435/69.1, 199; 930/240

[56] References Cited

PUBLICATIONS

Hattori et al., EMBL/GenBank Database Sequence Search Report Accession No. D11374, Submitted 04–Jun. 1992 to DDBJ.

Rudinger, In "Peptide Hormones", (ed. J.A. Porsons) University Park Press, Baltimore, Jun. 1976; pp. 1–7.

*Primary Examiner*—Paula K. Hutzell
*Assistant Examiner*—Robert C. Hayes
*Attorney, Agent, or Firm*—Foley & Lardner

[57] ABSTRACT

A cell division mechanism controlling protein which is not expressed during interphase but is expressed in the nucleus after entering into the cell cycle of a mammalian cell, fragments thereof, as well as DNAs coding for said protein or fragments thereof, as well as antibodies against said protein or fragment thereof.

5 Claims, 9 Drawing Sheets

Fig.1

```
SpanN   -7  GQGSRRRNYN NQEAGAAFMQ FLTLLLGDVVR LKGFESYRAQ LDTKTDSTGT HSLYTTYQDH
            ** **** **  . * .. ***  ** . * . *  * . . . *   ** *       * .  ..
GAP3m  203  GQTSEEELFS TNEESPAFVE FLEFLGQKVK LQDFXGFRGG LDVTHGQTGT ESVYCNFRNK SpanN   54  EIMFHVSTML PYTPNNQQQL LRKRHIGNDI VTIVFQEPGS KPFCPTTIRS HFQHVFLVVR
            ********   ... *  *******  . * . . *    *        * .. * *
GAP3m  263  EIMFHVSTKL PYTEGDAQQL QRKRHIGNDI VAVVFQD-EN TPFVPDMIAS NFLHAYVVVQ SpanN  114  AHAPCTPHTS YRVAVSRTQD TPAFGPALPE GGGPFAANAD FRAFLLAKAL NGEQAAGHAR
            . .  .      * . * .   . * .  * *  *** *        * . .  *   ** . *
GAP3m  413  AEGGGPDGPL YKVSVTARDD VPFFGPPLPD -PAVFRKGPE FQEFLLTKLI NAEYACYKAE SpanN  174  QFHAMATRTR QQYLQDLATN EVTTTSLDSA SRFGLPSLGG RRRATPRSPG ADVQAAGALM
            . * ..*. *  . .  ..*                           .
GAP3m  473  KFAKLEERTR AALLETLYEE LHIHSQSMMG LGGDEDKMEN GSGGGGFFES FKRVIRSRSQ
```

STRUCTURE OF SPA-1 PROTEIN

SPA-1 PROTEIN

CROSS REFERENCE TO RELATED APPLICATION

This application is a continuation-in-part application of Ser. No. 08/325,909 filed on Oct. 19, 1994, now abandoned.

TECHNICAL FIELD

The present invention relates to a SPA-1 protein involved in the control of cell division, and fragments thereof, genes coding therefor as well as antibodies against the protein.

BACKGROUND OF INVENTION

Lymphoid cells have unique properties in cell growth ability in comparison with many other somatic cells. Namely, lymphoid cells, similar to many other somatic cells, are differentiated from a hematopoietic stem cell to mature cells via many steps of cell division, and enter the interphase (G0/G1). After that, if they are stimulated with an antigen or a special growth factor, they again enter a cell cycle and increase to a clone with a redifferentiation, and then return to the interphase (memory cells). In addition to functional differentiation and expression specific to lymphoid cells, such repeated cell proliferation (clone proliferation) is one of the big factors in an immune response of an organism.

DISCLOSURE OF THE INVENTION

The present invention relates to a novel protein SPA-1 and fragments thereof expected to be involved in the control of said repeated cell growth, and fragments thereof, genes coding therefor, as well as antibodies against said proteins.

BRIEF EXPLANATION OF DRAWINGS

FIG. 1 compares an amino acid sequence of Span-N (SEQ ID NO:6) and an amino acid sequence of GAP3m protein (SEQ ID NO:7).

DETAILED DESCRIPTION OF THE INVENTION

The present invention relates to a protein which controls a mechanism of cell division and is not expressed in the interphase but is expressed in the nucleus after entering into a cell cycle, during the cell cycle of a mammalian cell.

Figure 2:
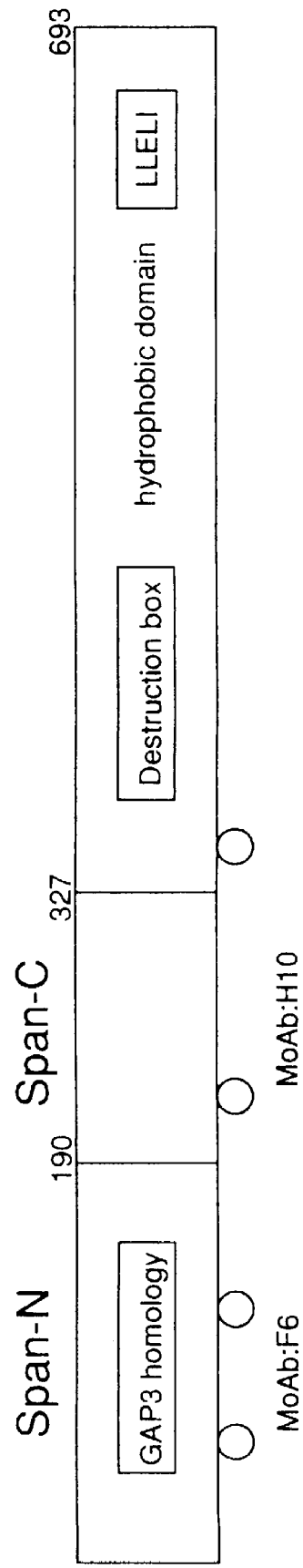
FIG. 2 schematically shows a structure of an SPA-1 protein.

This protein is designated SPA-1 and has a structure shown in FIG. 2. Namely SPA-1 comprises the N-terminal half thereof which may be further divided to Span-N positioned on the N-terminal side and having a high homology with GAP3 protein, and Span-C adjacent to the C-terminal of the Span-N and having a unique amino acid sequence.

An amino acid sequence deduced from a nucleotide sequence of cDNA starts with the first Met and ends at the 693rd Ala in SEQ ID NO.: 2. The Span-N has an amino acid sequence starting with the first Met and ends with the 190th Leu, and Span-C has an amino acid sequence starting with the 191st Ala and ends at the 327th Leu of SEQ ID NO:2.

However, polypeptides and proteins of the present invention are not limited to those described above, but those having small modification in a precise amino acid sequence while maintaining the activities of the present invention are included in the present invention. These modifications include replacement of one or more amino acids in the sequence with other amino acids, and addition or deletion of one or more amino acids, and these variations are included in the present invention as far as they maintain the activities of the present invention.

The addition, deletion and replacement of amino acids can be carried out according to site-specific mutagenesis well known prior to filing the present invention (for example, see Nucleic Acid Research Vol. 10, No. 20, p 6487 to 6500, (1982)), and regarding the addition, deletion and replacement of amino acids, "one or more amino acids" means, for example, those number of amino acids which can be added, deleted or replaced by site-directed mutagenesis.

The above-mentioned polypeptides or proteins can be produced by expressing a gene coding for said polypeptides or proteins according to a genetic engineering procedure. A gene coding for said polypeptides or proteins can be obtained as cDNA, genomic DNA or chemically synthesized DNA.

A cDNA coding for SPA-1 may be obtained from lymphocytes by cloning a gene which is not substantially expressed in the interphase (G0/G1 phase) but is expressed in the growth phase (S phase). For example, cDNA coding for SPA-1 can be obtained by preparing a cDNA preparation from lymphocytes in the G0/G1 phase and a CDNA preparation from lymphocytes in the S phase according to a conventional procedure, allowing these cDNA preparations to hybridize, and selecting cDNA from the S phase, which does not hybridize with cDNAs from the G0/G1 phase. An example of the concrete methods for cloning is described in Example 1(1).

A genomic DNA coding for SPA-1 can be obtained by constructing a genomic DNA library from a target animal, and screening the genomic DNA library using cDNA, for example a full length cDNA obtained as described above. A concrete process for the screening is described in Example 3. For example, a genomic DNA coding for SPA-1 is obtained as a 5.7 kbp BamHI fragment (designated Spa-GC2) and a 6.6 kbp BamHI fragment (designated Spa-GC9) of the genomic DNA.

Figure 6:
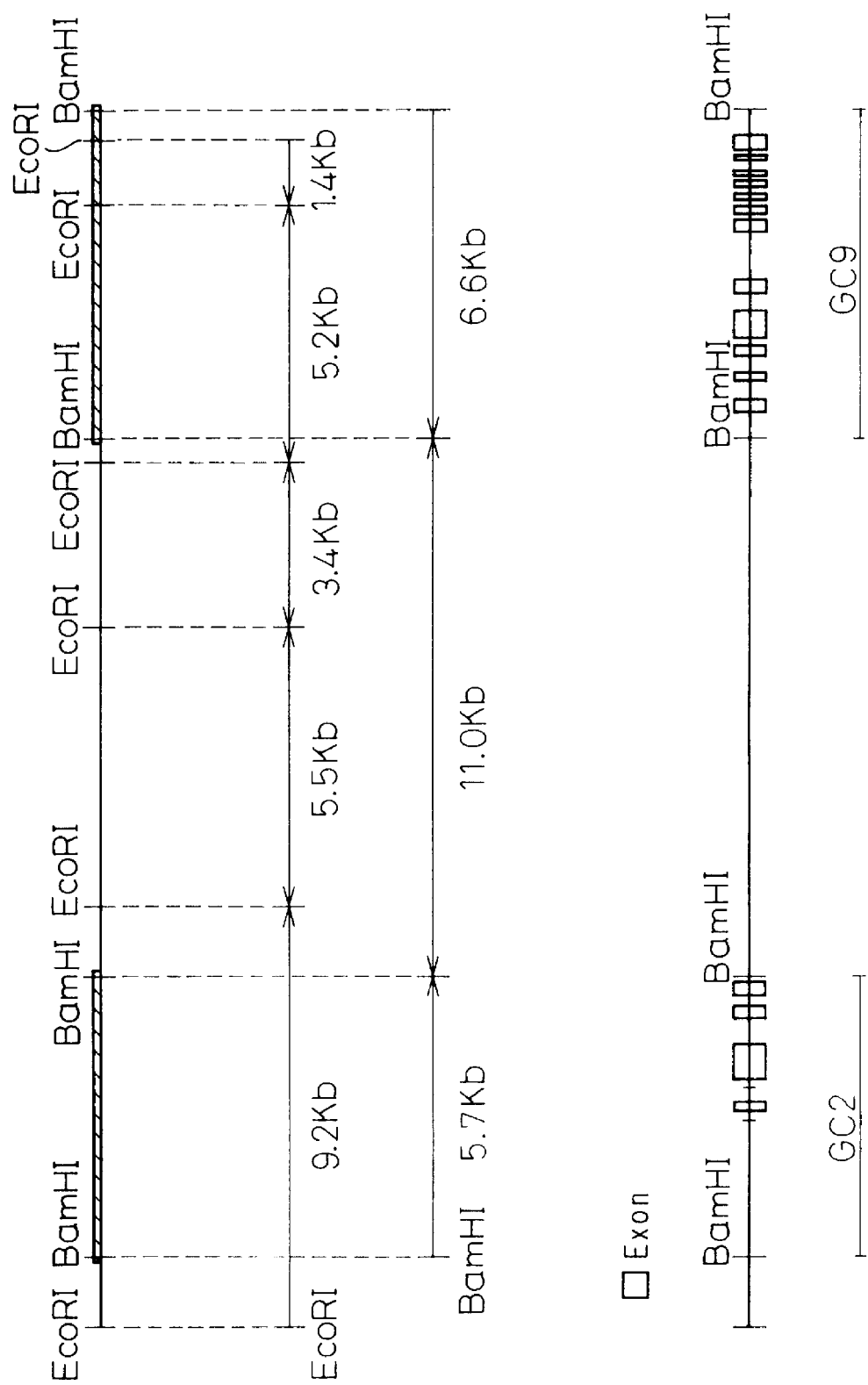
FIG. 6 shows a restriction enzyme map of a genomic DNA coding for SPA-1 of the present invention.

As shown in FIG. 6 as well as SEQ ID NO:3, the 5.7 kbp DNA fragment (Spa-GC2) contains 4 exons (exons 1 to 4) which exist in a region of about 2.5 kbp of the 3'-terminal side of the 5.7 kbp fragment. On the other hand, the 6.6 kbp fragment (Spa-GC9) contains 12 dispersed exons (exons 5 to 16) (SEQ ID NO:4). These exons 1 to 16 contain a full length of the above-mentioned cDNA. A coding region of the cDNA is contained in a region from the 3'-terminal half of the exon 5 to the 5'-terminal half of the exon 16.

According to the present invention, a DNA coding for SPA-1, or a fragment thereof such as Span-N or Span-C, can be obtained by treating the cDNA or genomic DNA prepared as described above with an exonuclease to eliminate an unnecessary portion, or cleaving the cDNA or genomic DNA with one or more appropriate restriction enzymes followed by supplementing a lacked portion with an oligonucleotide or eliminating a unnecessary portion. In addition, a gene coding for a polypeptide wherein one or more amino acids are lacked in the native amino acid sequence, one or more amino acids are added to the native amino acids sequence, and/or one or more amino acids in the native amino acid sequence are replaced with other amino acids can be obtained by subjecting said cDNA or genomic DNA to, for example, site-directed mutagenesis.

The present invention further includes DNA and RNA hybridizable with one of nucleotide sequences shown in SEQ ID NOs.: 1, 3 or 4. Such a hybridizable DNA or RNA preferably maintains a biological function of SPA-1, or a fragment thereof such as Span-N or Span-C. For example, the hybridizable DNA or RNA is that hybridizable with the above-mentioned cDNA or genomic DNA under the condition of, for example, 50% formamide, 5×SSC, 10% Na-dextran and 20 mM Na-phosphate (pH 6.5) at 42° C.

The present polypeptide or protein can be expressed in eukaryotic cells or prokaryotic cells according to a conventional procedure. The eukaryotic cells include cultured cells such as NIH3T3 cells, Cos-1 cells, CHO cells etc. of human or other animals, as well as enkaryotic microorganisms such as yeast, filamentous fungi. Yeast includes *Saccharomyces cerevisiae*) etc.; the filamentous fungi include the genus Aspergillus, such as *Aspergillus niger* etc. The prokaryotic organisms include bacteria. For example, Bacillus, such as *Bacillus subtilis, Escherichia coli* etc. are used.

To express said DNA in these hosts, an expression vector comprising a DNA containing said coding region, and an expression control region for said DNA is used. The expression control region used in the expression vector can be conventional one. For example, for expression in animal cells, a viral promoter such as LTR promoter, CMV promoter, SRα promoter etc. may be used; for expression in *E. coli,* T7 promoter, LacZ promoter etc. may be used; and as yeast promoter, for example, α-conjugation factor promoter can be used.

The present polypeptides or proteins can be obtained by culturing host cells transformed with an expression vector as described above, and recovering a desired polypeptide or protein from the culture. Transformation of host cells with an expression vector can be carried out depending on the nature of the host cells according to a conventional procedure. Culturing of the transformed cells also can be carried out according to a conventional procedure. Recovery and purification of a desired polypeptide from a culture are carried out according to a combination of conventional procedures used in purification of proteins including affinity chromatography, concentration, lyophilization etc.

EXAMPLES

The present invention is further explained in detail in the following Examples, but the scope of the invention is not limited to that of the Examples.

Example 1. Cloning and Characterization of SPA-1 cDNA (1) Cloning of SPA-1 cDNA

According to the present invention, first, a gene which is little expressed in the quiescent state (G0/G1 phase) but induced in the cycling state (S phase) of lymphocytes, was cloned by differential hybridization between a lymphoid cell line (LFD-14) in the quiescent state by starvation of interleukin 2 (IL-2) for 3 weeks (LFD-14⁻) and those in the cycling state by restimulation of IL-2 (LFD-14⁺). A cDNA library was constructed using poly (A)⁺RNA prepared from LFD14⁺ in a CDM8 cloning vector according to a conventional procedure (Aruffo, a., et al., Proc. Natl. Acad. Sci. USA, 84, 8573, (1987)). ($\alpha$-$^{32}$p) dCTP-labeled cDNA probes were synthesized from poly(A)⁺RNA's prepared from LFD-14⁻ and LFD-14⁺. Duplicate filters of the cDNA library were hybridized with each of above cDNA probes in hybridization buffer (5×SSC, 5×Denhardt's solution, 50 $\mu$g/ml salmon sperm DNA, 50 mM sodium phosphate, 0.1% SDS) at 65° C. overnight. Filters were washed with 0.1× SSC, 0.1% SDS at 65° C. before autoradiography. A cDNA clone, which was selectively detected by LFD-14⁺ probe, was designated SPA-1 and a vector comprising this CDNA was designated pcSPA-1. The SPA-1 CDNA can be isolated by cleaving said vector with a restriction enzyme Xho I.

(2) Structure of SPA-1 cDNA

The SPA-1 cDNA was sequenced according to a conventional procedure, and a result is shown in SEQ ID NO.: 1. This cDNA is about 3.5 kb in length, and has at the 5'-terminal side a long (about 1.2 kb) 5'-non-translation region containing a lot of short open reading frames (ORFs). This region is a strong translation-repressing region commonly found in certain oncogenes, showing that the SPA-1 gene is also strongly repressed at a level of translation.

This CDNA further comprises an open reading frame of about 2.1 kb starting from the 1200th nucleotide A (adenine) to the 3278th nucleotide C (cytosine) in SEQ ID NO.: 1. Among the amino acid sequence encoded by this open reading frame (SEQ ID NO:2), the N-terminal half (190 amino acid residues) (designated Span-N) has high homology with human Rap1GAP (GAP$_3$), and the C-terminal half (designated Span-C) has a novel sequence. The homology between the amino acid sequences of Span-N and GAP$_3$ is shown in FIG. 1.

(3) Preparation of Monoclonal Antibodies To Each Domain in SPA-1 N-Terminal Portion SPA-1 cDNA was cleaved with a restriction enzymes BglI and PstI to obtain a DNA fragment coding for Span-N and a DNA fragment coding for Span-C (about 140 amino acid residues). On the other hand, pGEX-1 vector (Pharmacia) was cleaved with PstI, blunt-ended using T$_4$ polymerase and EcoRI linkers were added to the blunted ends. The above-mentioned Span-N DNA fragment or Span-C DNA fragment was inserted into the EcoRI sites of the modified pGEX-1 vector to construct an expression plasmid pGEX-SpanN or pGEX-SpanC comprising a sequence coding for a fusion protein of the Span-N or Span-C and GST (glutathione-S-transferase), respectively. These expression plasmids were expressed in *E. coli,* and expression products were recovered and purified to obtain Span-N/GST fusion protein and Span-C/GST fusion protein respectively.

Then 200 $\mu$g of the fusion protein was mixed with Freund's complete adjuvant and the mixture was subcutaneously administered to immunize an Arumenia hamster (male, 5 weeks old). After that, 200 $\mu$g each of the fusion protein mixed with Freund's incomplete adjuvant was three times intraperitoneally administered to the hamster, at intervals of two weeks. After three days from the final immunization, the spleen was removed from the hamster, and minced to prepare a single cell suspension of the spleen. This suspension was subjected to a cell fusion with mouse myeloma cell line P3U1, according to the Leo, O et al. method (Proc. Natl. Acad. Sci. USA, 84: 1374, 1984), to obtain hybridomas.

Among the hybridomas, clones producing a desired antibody were selected with ELISA using corresponding fusion protein used to immunize the hamster. Namely, 1 μg/well of each fusion protein (GST-SpanN, or GST-SpanC) or 1 μg/well of GST protein alone was immobilized to a 96-well plate, and 100 μl of hybridoma supernatant was added into each well and allowed to react with the immobilized protein.

Figure 7:
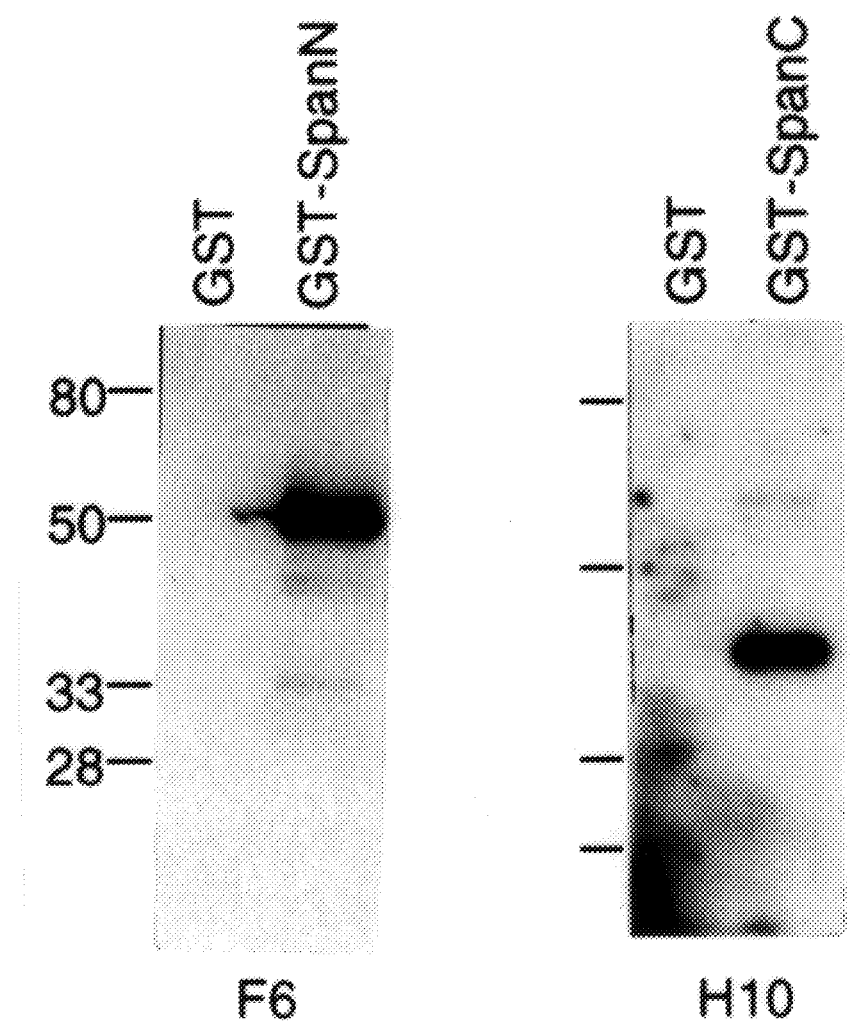
FIG. 7 shows a result of an electrophoresis showing the reactivity of monoclonal antibodies F6 and H10 to GST protein, GST-Span N and GST-Span C fusion proteins.

Then, anti-hamster IgG-peroxidase was added to the wells for reaction, followed by a substrate ABTS (2,2'-adino-di-3-ethyl-benzothianodino-6-sulfate) for coloring, and clones which react with the fusion protein but do not react with GST were selected as positive clones. Cells in the positive wells were cloned by limiting dilution method to obtain a clone from a single cell. A monoclonal antibody against Span-N is designated "F6", and monoclonal antibody against Span-C is designated "H10". FIG. 7 shows reactivity of each monoclonal antibody with fusion proteins, analyzed by Western blotting.

Namely, FIG. 7 shows a result obtained by the following method: 10 μg of GST-SpanN or GST-SpanC fused protein, or GST alone was separated by SDS-PAGE, blotted on a membrane, reacted with an F6 or H10 antibody solution (10 μg/ml), and detected with $^{125}$I-Protein A (Amersham).

Note, the hybridoma producing monoclonal antibody F6 was designated F6 and deposited with National Institute of Bioscience and Human-Technology Agency of Industrial Science and Technology as FERM BP-4839 on Oct. 18, 1994 under the Budapest treaty; and the hybridoma producing monoclonal antibody H10 was designated H10 and deposited with the National Institute of Bioscience and Human-Technology Agency of Industrial Science and Technology as FERM BP-4840 on Oct. 18, 1994, under the Budapest treaty.

(4) Detection of SPA-1 Protein By Monoclonal Antibody

Protein was extracted from cultured cells of lymphoid cell line LFD14 (Kubota, H. et al., J. Immunol. 145, 3924, 1990) according to a method of Harlow, E. et al., Mol. & Cellular Biology 6: 1579, 1986), and identified by immunoblotting using said monoclonal antibodies, immunoprecipitation method, immunostain method etc.

As a result, for example, a protein from lymphoid cell line LFD14 was detected as a band of a molecular weight of about 68 KDa in Western blotting using monoclonal antibody F6. From this result, it is expected that the SPA-1 gene encodes a nuclear protein of about 68 KDa.

Namely, it is expected that SPA-1 protein of the present invention has an amino acid sequence starting from the first amino acid methionine and ending at the 693rd amino acid alanine in SEQ ID NO: 1.

Figure 8:
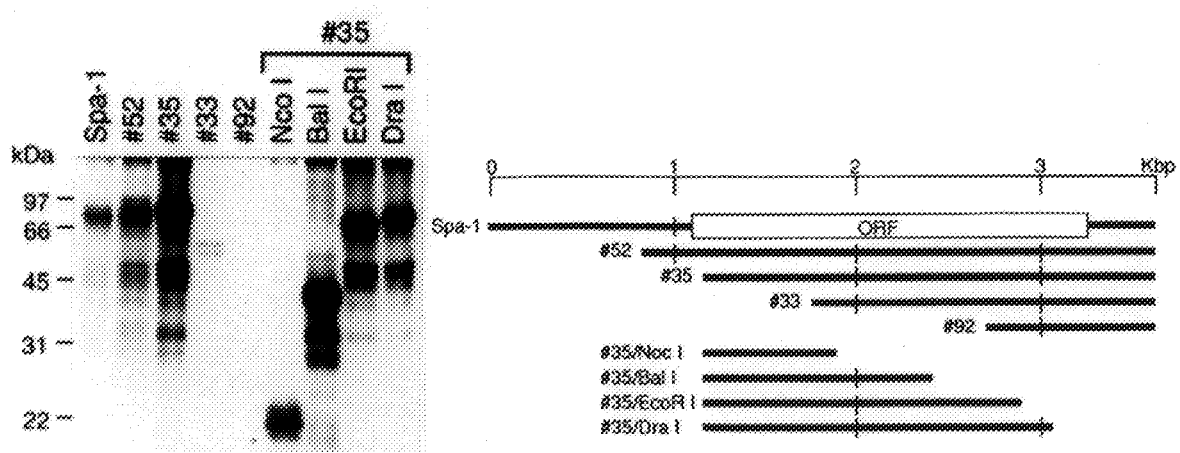
FIG. 8 shows a result of an electrophoresis showing a profile of expression products from SPA-1 genes lacking various regions.

Example 2. Expression of SPA-1 cDNA (1) Expression of SPA-1 Protein Expression By In Vitro Transcription/Translation FIG. 8 shows a result of an analysis of SPA-1 protein expressed by in vitro transcription/translation method using various lengths of SPA-1 CDNA as a template. As shown in FIG. 8, pBluescript Ks$^+$-SPA-1 plasmid containing a full length SPA-1 CDNA, clones (#52, #35, #33, and #92) lacking 5'-terminal portion of said SPA-1 cDNA in different length, and plasmids containing a full length ORF but lacking 5'-non-translational region which negatively acts on the translation upwards from the different positions (NcoI (1928), BalI (2229), EcoRI (2879), or DraI (3035)) downstream of the plasmid #35 were used as a template.

Using 10 μg of these template DNAs, complementary mRNAs (cRNAs) were synthesized with an RNA transcription kit (Stratagene). These cDNAs were in vitro translated in the presence of $^{35}$S-methionine (Amersham) according to the Tagawa et al. method (J. Biol. chem. 256: 20021, 1990) using an in vitro expression translation kit (Promega). The translation product was immunoprecipitated with the abovementioned H10 antibody and protein A beads (Pharmacia), and the precipitate was analyzed by SDS-PAGE.

As a result, where full length pBluescript-KS$^+$-SPA-1, #52 and #35 plasmids completely containing ORF and 3'-non-translational region were used as templates, a specific band of about 85 KDa was detected, while where plasmid (#33) lacking a part of the ORF was used a translation product shortened (about 50 KDa) corresponding to the lack of the ORF was detected. In addition, where plasmids (#35/BalI, #35/EcoRI, and #35/DraI) lacking 3'-non-translation region were used, translation products shorter than 85 kDa corresponding to an extent of lacking were obtained.

These results show that the SPA-1 protein is a polypeptide starting from the first amino acid methionine and ending at the 693rd amino acid alanine encoded by a nucleotide sequence started with the 1200th nucleotide A and ending at the 3278th nucleotide C in SEQ ID NO: 1.

Expression By Stable Animal Cell Transfectant

The SPA-1 cDNA was obtained by cleavage of plasmid SPA-1 with restriction enzymes BglI and DraI, and inserted into EcoRI site of pSRα expression vector (Takebe, Y. et al., Mol. Cell Biol., 8: 466–472, 1988) to construct an expression plasmid SRa-SPA-1, which was then co-introduced into NIH3T3 cells (ATCC CRL-1658) together with a plasmid pSV$_2$NeO and transfected cells were selected by G418 to obtain a stable transfectant (NIH/SPA-1 cells).

Figure 9A:
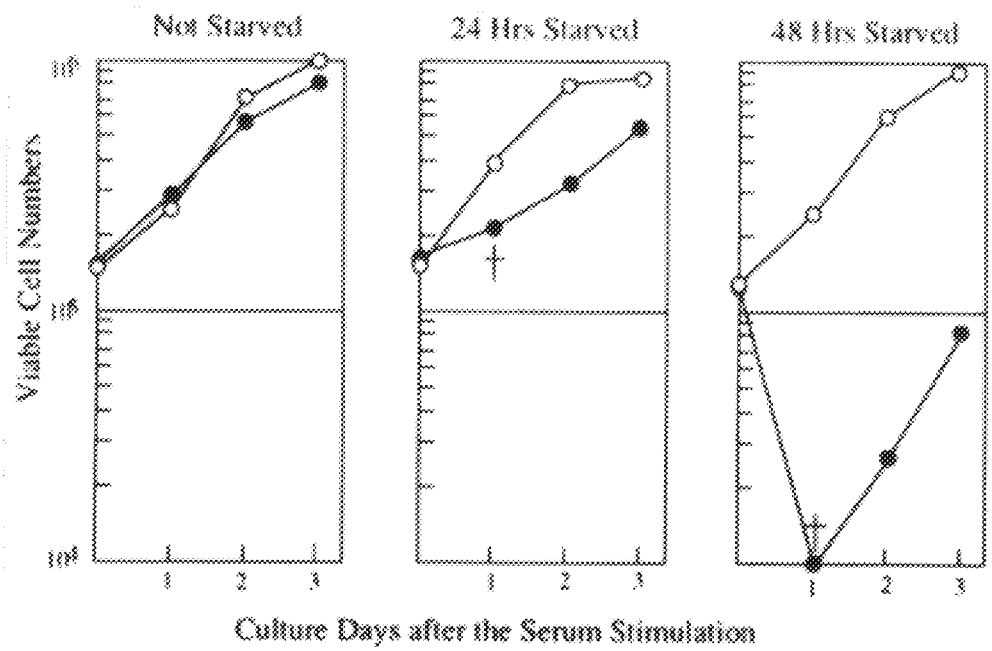
FIGS. 9a and 9b are micrographs showing the effects of the overexpression of SPA-1 gene in animal cells on the cell growth when the growth of said animal cells is synchronized by serum-starvation and addition of serum.
Figure 9B:
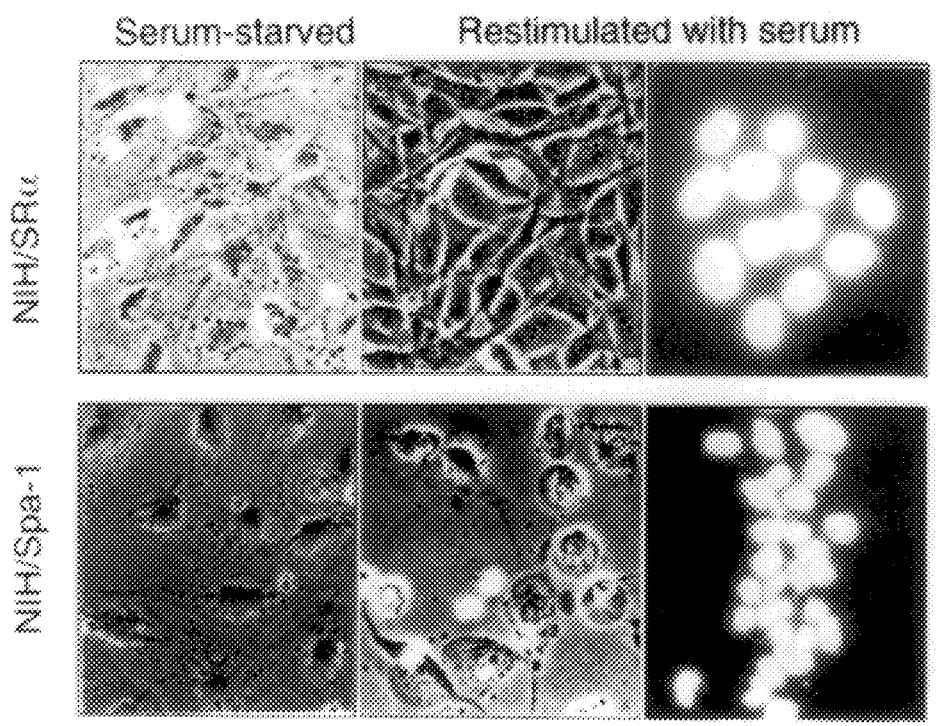
Figure 10A:
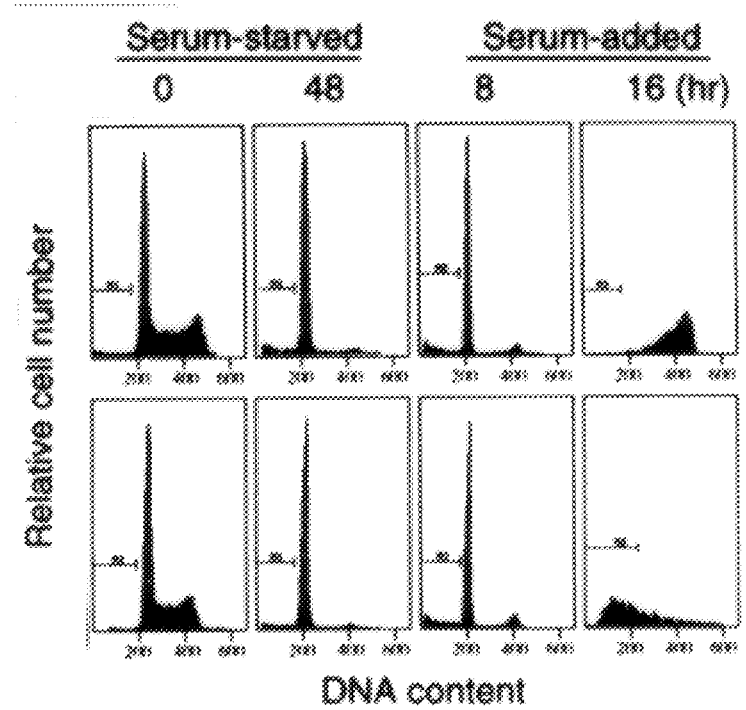
FIGS. 10a, b and c are micrographs showing the effects of overexpression of a SPA-1 gene introduced into animal cells on the cell growth when the growth of said animal cells is synchronized by serum-starvation and addition of serum.
Figure 10B:
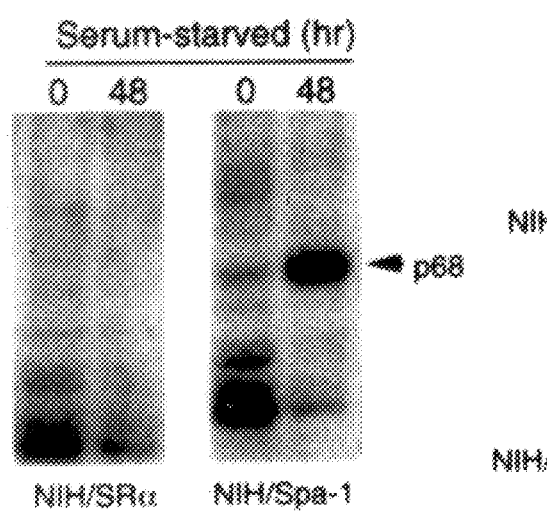

As shown in FIG. 9A, the NIH/SPA-1 cells grew under a usual culture condition (supplemented with 5% serum) in a manner not different from control cells, i.e., NIH3T3 cells to which SRα vector alone had been introduced do. However if the same cells were cultured in a serum-reduced condition (0.5% serum) to synchronize them to the G1 phase (extended G1) and after a certain time later the cells were restimulated with serum to reenter the cell cycle, they rapidly died off in the middle to end of the S phase (FIG. 10A). Morphologically, the cells became round up, and remarkable nuclear condensation was observed, and therefore it was considered that so-called mitotic catastrophes occurred (FIG. 9B). In addition, SPA-1 exhibits a unique change of expression along with synchronization of cell cycle, suggesting that expression thereof, similar to cyclines, is controlled by cell cycle (FIG. 10, B and C).

FIG. 9 shows induction of the death of cells by growth stimulation after blocking the $G_1$ phase of cell cycle, in NIH3T3 cells (NIH/SPA-1) transfected with SPA-1 cDNA. FIG. 9A shows a result obtained by culturing the NIH/SPA-1 cells (●) and the NIH-SRA cells (0) prepared by introducing pSRa vector alone into NIH3T3 cells in the presence of 5% serum to an almost confluent state, transferring the cells to a medium containing 0.5% serum, and after culturing the cells for 0, 24 or 48 hours, transferring the cells to a medium containing 20% serum so as to count the number of cells as time elapses.

FIG. 9B shows micrographs of NIH/SRI cells and NIH/SPA-1 cells cultured in the presence of 0.5% serum for 48 hours and then in the presence of 20% serum for 18 hours.

The right shows the morphology of the nucleus of the cell at that time, in Hoechst 33427 (Sigma). The shrink of the nucleus was observed in NIH/SPA-1.

In FIG. 10, A shows a result of analysis of cell cycle in NIH/SPA-1; the upper portion relates to NIH/SRI cells and the lower portion relates to NIH/SPA-1 cells. After 16 hours from the addition of serum, NIH/SPA-1 cells had died (control cells had entered to the S phase). FIG. B shows an accumulation of SPA-1 protein in a serum-free culture ($G_1$ arrest). For NIH/SPA-1 cells, although the transfected SPA-1 mRNA was detected, under a usual condition (lane of oh) SPA-1 gene was not substantially detected by Western blotting (probably due to constant degradation). However, where a serum concentration was reduced to 0.5% to maintain the cell cycle at the $G_1$ phase ($G_1$ arrest), accumulation of SPA-1 protein was observed.

Figure 10C:
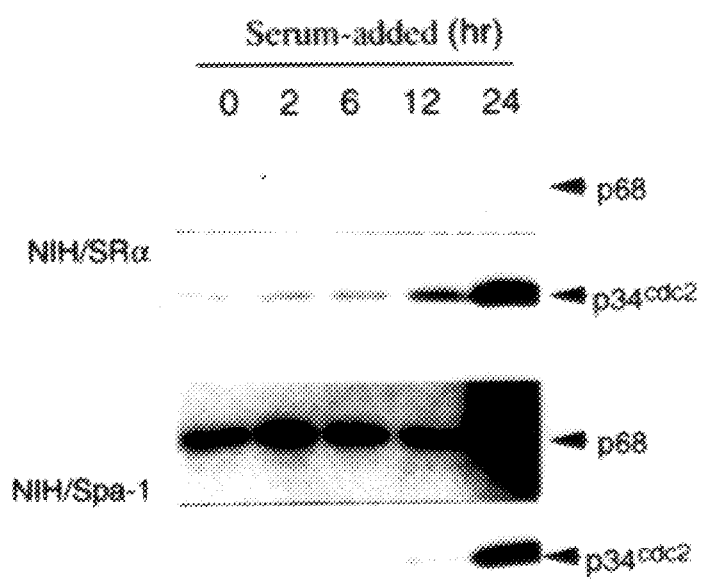

FIG. 10C shows the kinetic change of SPA-1 protein after the addition of serum. After the $G_1$ arrest for 48 hours, the cell cycle was started by the addition of serum, then only living cells were recovered at each time and SPA-1 protein was detected. A part of NIH/SPA-1 cells survived after the addition of serum for 24 hours, and in these cells the increase of cdc2 expression was observed. On the other hand, at this point, SPA-1 protein had already decreased.

Expression Of Recombinant SPA-1 In *E. coli*

The SPA-1 cDNA was cleaved with a restriction enzyme BglI (which cleaves at the 1171st nucleotide) and a restriction enzyme DraI (which cleaves at the 3038th nucleotide) to obtain a BglI-DraI fragment, which was then blunt-ended with T4 polymerase. This DNA fragment was ligated to EcoRV-cleaved plasmid BS-SK (Transgene) to obtain a plasmid SK⁺-SPA-1. Next, this plasmid was cleaved with Hind III, and to the resulting Hind terminals were added BamHI linkers, and the BamHI linkers were cleaved with BamHI to obtain a BamHI fragment, which was inserted into BglII-digested expression plasmid pET-16b (Novagen, USA) to obtain an expression plasmid pET-SPA1. This plasmid was used to transform *E. coli*.

By culturing the *E. coli*, subjecting an expression product from the culture to electrophoresis, and detecting the product by the above-mentioned monoclonal antibody F6, a band corresponding to a molecular weight of 85 KDa was detected and expression of recombinant SPA-1 (rSPA-1) was confirmed.

Figure 3:
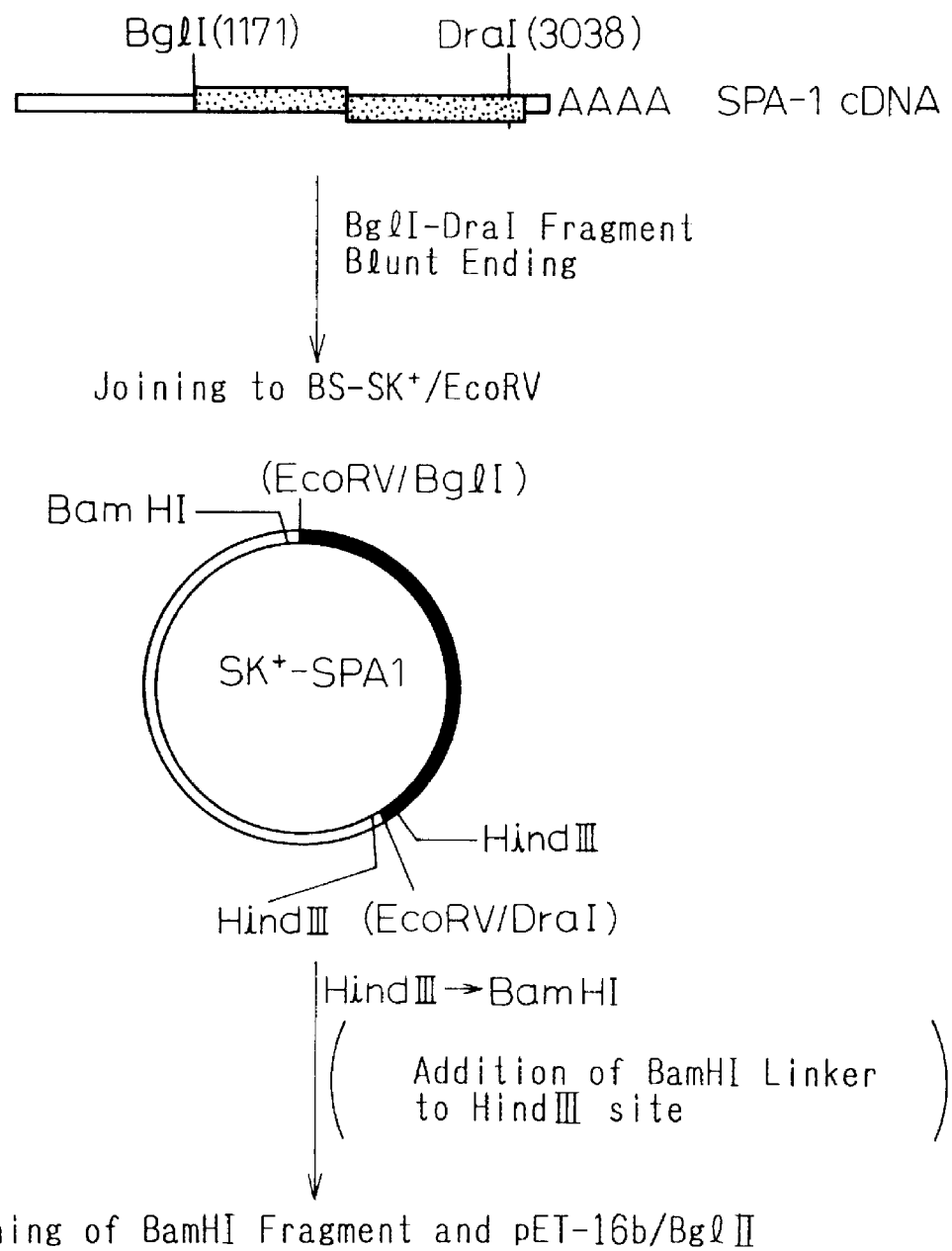
FIG. 3 shows a process for construction of a recombinant expression plasmid for SPA-1 protein.

A process for construction of the expression plasmid pET-SPA-1 is shown in FIG. 3.

(2) Physiological Activities of Span-N

Since Span-N has homology with GAP3, GAP activity of the above-mentioned GST-SpanN fusion protein was tested. As a control, a fusion protein of human GAP3 (75th to 663rd amino acid residues) and GST was used. The effects of these fusion proteins on GTPase activity of yeast Rsr1 (1st to 272nd residues), human Rap1A ($Glu^{63}$) (1st to 184th residues), human Ha-Ras (1st to 189th residues) and a human RhoA (1st to 193 residues) GST fusion protein (Nur-E-Kamal et at., Mol. Biol. Cell 31, 1437–1442, 1992; Nur-E-Kamal et al., J. Biol. Chem. 267, 1415–1418, 1992) was investigated according to the Maruta et al. method (J. Bio. Chem. 266: 11661–11668, 1991). As a result, it was shown that although the Span-N was not effective to Ha-Ras, Rac1, Rho1 etc., it has selective GAP activity to Rap1 and Rsr1.

TABLE 1

Activation of GTPase activity of Rsr1, Rap1, etc. by Span-N or GAP3m

| smG Protein | Native GTGPase activity (Turn over/min.) | Stimulation (times) Span-N | GAP3m |
|---|---|---|---|
| Rsr1 | 0.001 | 16.0 | 7.0 |
| Ral1A($Glu^{63}$) | 0.0015 | 6.0 | 10.0 |
| Ha-Ras | 0.022 | 0.3 | 0 |
| RhoA | 0.060 | 0.6 | 0 |
| Rac1 | 0.090 | 0 | |

Figure 4:
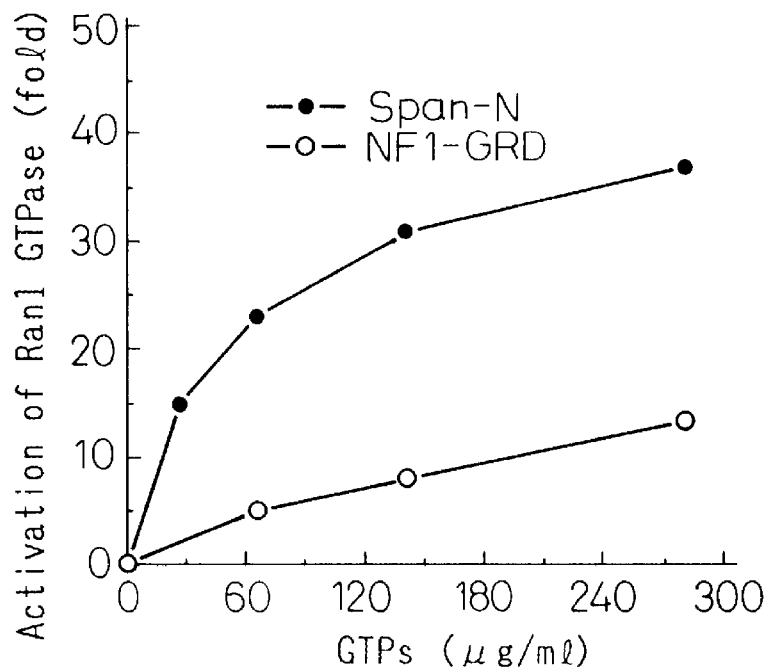
FIG. 4 is a graph showing that Span-N activates Ran1 GTPase in a dose dependent manner.

In addition, the relationship between Span-N concentration and Rsr1 GTPase activity is shown in FIG. 4. The Figure shows that Rsr GAP activity of Span-N depends on its concentration. Note that GAP activity was measured according to the Maruta et al. method (J. Biol. Chem. 266: 11661–11668, 1991).

SPA-1 is a nuclear protein, while there is no report that Rap1 exists in the nucleus. Therefore, activity of Span-N etc. to the sole low molecular weight G protein, Ran, known to be present in nucleus was studied. As a result, it was shown that Span-N exhibits a clear GAP activity on Ran. This result is shown in Table 2.

TABLE 2

Activation of Ran GTPase by Span-N and other GAPs

| GAPs | $EC_{16}$ (μg/ml) |
|---|---|
| SPA-1(Span-N) | 25 |
| GAP3m(Rap GAP) | 130 |
| p190C(Rho GAP) | 150 |
| NF1-GDR(Ras GAP) | 300 |

Figure 5:
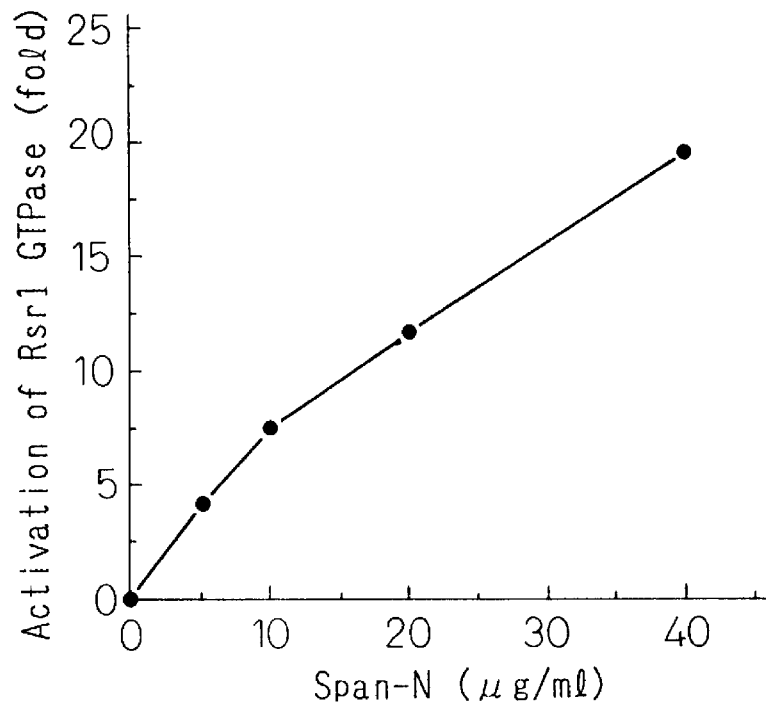
FIG. 5 is a graph showing that Span-N activates Rsr1 GTPase in a dose dependent manner.

In addition, FIG. 5 shows the relationship between Span-N concentration and Ran GTPase activity.

Example 3. Cloning of Genomic Gene (1) A mouse genomic library (EMBL3-Adult DBA/2J liver DNA:CLONTECH, ML 1009d) comprising $1.0 \times 10^6$ clones was blotted on Hybond-N⁺ membranes (Amersham, RPN 303B). A vector SPA-1 cDNA/pBluescript incorporating a SPA-1 cDNA was cleaved with XhoI (Toyobo, XHO-101) to obtain a full length SPA-1 cDNA, which was then labeled with $^{32}$p-dCTP (Amersham, PB0205) using a Nick Translation Kit (Amersham, N5000).

This probe was reacted with the above-mentioned genomic library in the presence of Rapid Hybridization Buffer (Amersham, RPN1636). As a primary screening, 15 positive or pseudopositive signals were obtained. As a secondary screening 9 positive clones were obtained. These were further screened so as to confirm all of the 9 strains were cloned. Genomic DNA in these clones are designated GC1 to GC9, respectively.

(2) Preparation of Mouse Total DNA

First 2 cm of the tail of a Bal b/c mouse of 4 weeks old was cut off, and was put into 1.5 ml Epptendolf tube. Then the cut tail was sliced with scissors. In this tube were added 500 μl of a mixed solution (439 μl of 1×SSC, 5 μl of 1M Tris-HCl (pH 7.5) and 1 μl of 0.5M EDTA (pH 8.0)), 50 μl of 10% SDS, and 5 μl of 20 mg/ml proteinase K, and the mixture was incubated at 37° C. for 12 hours.

Next, 500 μl of buffered phenol was added thereon, and the whole was gently mixed for 5 minutes. The mixture was centrifuged at 10,000 rpm, at a room temperature for 5 minutes. The liquid phase was transferred into a fresh Epptendorf tube, and 700 µl of isopropanol was added thereon, and the tube was reversed a few times to generate fibrous precipitate.

This precipitate was transferred to a fresh tube into which 500 µl of 70% ethanol had been introduced, and after removing the 70% ethanol, the precipitate was washed with 100% ethanol. The precipitate was dried with dry air and 100 µl of TE buffer was added thereon to prepare a total DNA.

(3) Screening of Genomic DNA Coding For SPA-1

The total DNA prepared in the section (2) was cleaved with BamHI (Toyobo, BHA 102) or EcoRI (Toyobo, ECO-101), blotted on Hybond-N$^+$ membranes, and screened by hybridization with the full length SPA-1 cDNA probe prepared in the above section (1). The hybridization was carried out in Rapid Hybridization Buffer as described in the section (1).

As a result, 5.7 kb and 6.6 kb BamHI fragments as well as 9.2 kb, 5.2 kb and 1.4 kb EcoRI fragments were positive. The 5.7 kb and 6.6 kb BamHI fragments contained a full length of SPA-1 cDNA and corresponded to the above-mentioned genomic fragments Spa-GC2 and Spa-GC9. Phage vectors comprising these genomic fragments were designated Spa-GC2/EMBL-3 and Spa-GC9/EMBL-3, respectively.

(4) Sequencing

These viral vectors were prepared and cleaved with BamHI, and using a Gene Clean Kit (Funakoshi) a 5.7 kb BamHI fragment from Spa-GC2/EMBL-3 and a 6.6 kb BamHI fragment from Spa-GC9/EMBL-3 were prepared respectively.

Next, each of these fragments was inserted into pBluescript II SK(+) (Toyobo SC212205) at its BamHI site using a DNA Ligation Kit (Takara 6021) and subcloned. Then deletion mutants were prepared by Kilo-Sequence Deletion Kit (Takara, 6030), and sequencing was carried out using a 7-deaza Sequenase (Toyobo, US 70777). As a result, it was founded that the Spa-GC2 contains exons 1 to 4 in its 3'-terminal half, and the Spa-GC9 contains dispersed exons 5 to 16.

The nucleotide sequence of Spa-GC2 is shown in SEQ ID NO.: 3, and the nucleotide sequence of Spa-GC9 is shown in SEQ ID NO.: 4. In the Spa-GC9, an amino acid coding region in cDNA is contained in a region from the 3'-terminal half of the exon 5 to the 5'-terminal half of the exon 16 (SEQ ID NO:5).

Note that FIG. 6 shows relative positions of the genomic fragments including Spa-GC2 and Spa-GC9.

It was suggested that the SPA-1 protein participates in the regulation of DNA replication and cell division because the protein strongly expressed after the S phase in the cell cycle of normal lymphocyte. On the other hand, it was shown that the said protein contains a Ran GAP activity domain at its N-terminal portion. The Ran is the sole low molecular weight G protein present in the nucleus and is associated with RCC-1 which is a GDP-GTP exchanger of Ran GTPase. RCC-1 is a nuclear protein well conserved in all cells from yeast to mammal, and is well known as a protein participating in check mechanism of entering into the $G_2$/M phase (namely, prevention of premature cell division prior to completion of DNA replication). In addition, recently it has been found that the RCC-1 gene precipitates in various aspects of cell nucleus functions including initiation of DNA replication, extranuclear transport of RNA, etc.

The RCC-1/Ran system is, however, constitutionally expressed regardless of the cell cycle. Accordingly, for long time, an intervention of a cell cycle-dependent factor, especially GAP molecule as an entity which links the cell cycle and RCC-1/Ran is expected. However, its true entity has not been clear. The finding in the present invention strongly suggests that SPA-1 is in fact the intervenient entity. In addition, it was found in the present invention that an over-expression of SPA-1 causes the mitotic catastrophes. This finding suggests that SPA-1 is a central molecule responsible for cell cycle-dependent control of the RCC-1/Ran system.

A mechanism by which the SPA-1 micro-regulates the RCC1/Ran system which represses cyclin/cdc 2 system driving DNA synthesis and cell division is an important object to be solved in future. Especially, the fact that the SPA-1 is highly expressed in lymphoid cells having unique cell growth properties suggests that the SPA-1 plays an important role in a growth control of the lymphoid cells and checking mechanism thereof.

Accordingly, the present protein is promising as differentiation control agent of lymphocytes. In addition, the present protein may be useful as an anti-tumor agent because if the present protein is expressed in tumor cells, it may induce the death of cells at the S phase of the cell cycle.

We claim:

1. An isolated, purified cell division mechanism controlling SPA-1 protein that is expressed during cell division in the nucleus and not expressed during interphase ($G_0/G_1$) of the cell cycle, wherein said protein exhibits GTPase activity on Ran, exhibits GTPase activity against Rap1A (Gln$^{63}$) and Rsr1, and does not substantially exhibit GTPase activity against Ha-Ras, Rac1, and Rho1, wherein said SPA-1 protein has the amino acid sequence of SEQ ID NO: 1.

2. A fragment of the SPA-1 protein selected from the group consisting of the Span-N protein fragment (amino acid residues 1–190 of SEQ ID NO:2) and the Span-C protein fragment (amino acid residues 191–327 of SEQ ID NO:2).

3. A Span-N protein fragment according to claim 2, having the amino acid sequence of amino acid residues 1–190 of SEQ ID NO:2.

4. A Span-C protein fragment according to claim 2, having the amino acid sequence of amino acid residues 191–327 of SEQ ID NO:2.

5. An isolated, purified SPA-1 protein encoded by a nucleotide sequence whose complementary strand hybridizes with SEQ ID NO: 1 under the following conditions:

50% formamide, 5×SSC, 10% Na-dextran, and 20 mM Na-phosphate (pH 6.5) at 42° C., wherein said protein exhibits GTPase activity on Ran, exhibits GTPase activity against Rap1A (Gln$^{63}$) and Rsr1, and does not substantially exhibit GTPase activity against Ha-Ras, Rac1, and Rho1.

* * * * *

UNITED STATES PATENT AND TRADEMARK OFFICE
CERTIFICATE OF CORRECTION

PATENT NO.    : 5,831,024
DATED         : November 3, 1998
INVENTOR(S)   : Nagahiro Minato et al.

It is certified that error appears in the above-identified patent and that said Letters Patent is hereby corrected as shown below:

<u>Title page,</u>
Item [30], Foreign Application Priority Data, please add the following:
-- Oct. 20, 1994 [JP] Japan...6-279712 --.

Signed and Sealed this

First Day of July, 2003

JAMES E. ROGAN
*Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 3519 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1200..3278

( x i ) SEQUENCE DESCRIPTION: SEQ ID NO:1:

| | | | | | | |
|---|---|---|---|---|---|---|
| GTCCTGCATG | CAGCTGCCCC | AGGAGCTCCT | GTGTCCTTGA | GGCCCATCTG | AACAGCCCCC | 60 |
| TCCTCTGCAG | TGCAGAAACC | ACTGAAGCCT | CAGCCTTCTG | GGTGGGCACC | AAGGACCCGT | 120 |
| GCCCACCAAT | GCGGCCCGGC | CCCCAGAGAG | TCAGGCCCAC | AGGAGCACGC | CCATGTGGGC | 180 |
| CGGAGGTGTG | GGGAGCCCTC | GGCGGGCATG | GCCCCTGCAC | CTACCGATGA | CCTCTTTGCC | 240 |
| CGTAAGCTTC | GCCAACCTGC | CCGGCCCCCA | CTGACACCAC | AATACCTTTG | AGCCGAGGCC | 300 |
| AGCTCGGGGC | CCACTCTTGC | GCAGTGGCAG | TGATGCTGGT | GAAGTCCGGC | CCCCTACACC | 360 |
| AGCCAGCCCC | CGTGCCCGTG | CCCACAGCCA | CGAGGATGCC | AGCCGCCCTG | CTGCAACCCC | 420 |
| TACTCGGCTC | TTCACTGACC | CACTGGCACT | GCTAGGGTTG | CCAGCAGAAG | AGCCAGAGCC | 480 |
| CACCTTCCCG | CCAGTGCTGG | AACCCCGGTG | GTTTGCTCAC | TATGATGTGC | AGAGCTTGCT | 540 |
| CTTTGACTGG | GCTCCACGAC | CTCGGGGGAC | AGGCAGCCAT | ACAGAGGCAA | ACTCTGGGAC | 600 |
| CTTAGCTGAG | GGCCAGACTA | CCACCTCAGA | TCTACTGCTC | GGGGCACCTG | GCTTTGTGAG | 660 |
| CGAGCTTGGT | GGTGAGGGTG | AGCTAGGGCT | GGGTGGGCCA | ATATCCCCAC | CTGTGCCCCC | 720 |
| TGCACTGCCT | AATGCGGCTG | TGTCCGTCCT | GGAGGAGCCA | CAGACCCGGA | CCACACTTAC | 780 |
| AGCCTGGAGC | ACGCAGATCT | GGGTGCAGGC | TACTACCGCA | AGTACTTCTA | TGGCAAAGAA | 840 |
| CACCAGAACT | TCTTTGGGTT | GGATGAGGCG | CTGGGTCCGG | TGGCCGTGAG | CCTGCGACGG | 900 |
| GAGGAGAAAG | AGGGCAGCGG | AGGGGGCACC | TACACAGCTA | CCGGGTCATC | GTGCGGACCA | 960 |
| CGCAGCTCCG | GACCCTCCGT | GGCACCATCT | CGGAGGACGC | ACTGCCTCCC | GGCCCCCCGA | 1020 |
| GCGTATCTCC | GAGGAAGCTT | CTGGAACATG | TGCTCCACGG | CTGAGCCCAC | CTGCCTGCGC | 1080 |
| CTGGGTTCAG | CCTCTCCCAA | GGTGCCCCGC | AGCTGCTTAC | TCTGGATGAG | CAAGTGCTGA | 1140 |
| GCTTCCAACG | CAAGGTGGGC | ATCCTGTACT | GCCGCGCAGG | CCAGGGCTCT | GAGGAAGAG | 1199 |

| | | | | | | | | | | | | | | | | |
|---|---|---|---|---|---|---|---|---|---|---|---|---|---|---|---|---|
| ATG | TAC | AAC | AAC | CAG | GAG | GCC | GGA | GCA | GCC | TTT | ATG | CAG | TTC | CTT | ACT | 1247 |
| Met | Tyr | Asn | Asn | Gln | Glu | Ala | Gly | Ala | Ala | Phe | Met | Gln | Phe | Leu | Thr | |
| 1 | | | | 5 | | | | | 10 | | | | | 15 | | |
| TTG | CTG | GGT | GAT | GTG | GTG | CGA | CTC | AAA | GGC | TTT | GAA | AGT | TAC | CGG | GCC | 1295 |
| Leu | Leu | Gly | Asp | Val | Val | Arg | Leu | Lys | Gly | Phe | Glu | Ser | Tyr | Arg | Ala | |
| | | | 20 | | | | | 25 | | | | | 30 | | | |
| CAG | CTG | GAT | ACC | AAA | ACG | GAT | TCC | ACG | GGC | ACA | CAC | TCA | CTC | TAC | ACC | 1343 |
| Gln | Leu | Asp | Thr | Lys | Thr | Asp | Ser | Thr | Gly | Thr | His | Ser | Leu | Tyr | Thr | |
| | | | 35 | | | | | 40 | | | | | 45 | | | |
| ACC | TAC | CAA | GAC | CAT | GAG | ATC | ATG | TTT | CAC | GTG | TCC | ACG | ATG | CTG | CCT | 1391 |
| Thr | Tyr | Gln | Asp | His | Glu | Ile | Met | Phe | His | Val | Ser | Thr | Met | Leu | Pro | |
| | 50 | | | | | 55 | | | | | 60 | | | | | |
| TAC | ACG | CCT | AAT | AAC | CAG | CAA | CAG | CTC | CTG | AGG | AAG | CGT | CAT | ATC | GGC | 1439 |
| Tyr | Thr | Pro | Asn | Asn | Gln | Gln | Gln | Leu | Leu | Arg | Lys | Arg | His | Ile | Gly | |
| 65 | | | | | 70 | | | | | 75 | | | | | 80 | |
| AAC | GAT | ATT | GTG | ACC | ATC | GTG | TTC | CAG | GAG | CCC | GGT | AGC | AAG | CCC | TTC | 1487 |
| Asn | Asp | Ile | Val | Thr | Ile | Val | Phe | Gln | Glu | Pro | Gly | Ser | Lys | Pro | Phe | |
| | | | | 85 | | | | | 90 | | | | | 95 | | |
| TGC | CCT | ACA | ACA | ATC | CGC | TCT | CAC | TTC | CAG | CAC | GTT | TTC | TTG | GTG | GTG | 1535 |
| Cys | Pro | Thr | Thr | Ile | Arg | Ser | His | Phe | Gln | His | Val | Phe | Leu | Val | Val | |
| | | | 100 | | | | | 105 | | | | | 110 | | | |
| CGT | GCG | CAT | GCT | CCC | TGC | ACC | CCA | CAC | ACC | TCA | TAC | AGG | GTG | GCA | GTG | 1583 |
| Arg | Ala | His | Ala | Pro | Cys | Thr | Pro | His | Thr | Ser | Tyr | Arg | Val | Ala | Val | |
| | | | 115 | | | | | 120 | | | | | 125 | | | |
| AGC | CGC | ACC | CAG | GAC | ACT | CCT | GCC | TTC | GGG | CCT | GCG | CTG | CCA | GAA | GGC | 1631 |
| Ser | Arg | Thr | Gln | Asp | Thr | Pro | Ala | Phe | Gly | Pro | Ala | Leu | Pro | Glu | Gly | |
| | | | 130 | | | | | 135 | | | | | 140 | | | |

-continued

| | | | | | | | | | | | | | | | | |
|---|---|---|---|---|---|---|---|---|---|---|---|---|---|---|---|---|
| GGA | GGC | CCC | TTT | GCA | GCC | AAT | GCC | GAT | TTC | CGG | GCC | TTT | CTG | TTG | GCT | 1679 |
| Gly | Gly | Pro | Phe | Ala | Ala | Asn | Ala | Asp | Phe | Arg | Ala | Phe | Leu | Leu | Ala | |
| 145 | | | | 150 | | | | | 155 | | | | | | 160 | |
| AAG | GCA | CTC | AAT | GGT | GAG | CAA | GCG | GCT | GGT | CAT | GCA | CGC | CAG | TTC | CAC | 1727 |
| Lys | Ala | Leu | Asn | Gly | Glu | Gln | Ala | Ala | Gly | His | Ala | Arg | Gln | Phe | His | |
| | | | | 165 | | | | | 170 | | | | | 175 | | |
| GCC | ATG | GCT | ACA | CGC | ACA | CGC | CAA | CAG | TAC | CTG | CAG | GAC | CTG | GCT | ACT | 1775 |
| Ala | Met | Ala | Thr | Arg | Thr | Arg | Gln | Gln | Tyr | Leu | Gln | Asp | Leu | Ala | Thr | |
| | | | 180 | | | | | 185 | | | | | 190 | | | |
| AAT | GAA | GTG | ACC | ACT | ACT | TCG | CTG | GAC | TCG | GCT | TCG | CGG | TTT | GGC | CTG | 1823 |
| Asn | Glu | Val | Thr | Thr | Thr | Ser | Leu | Asp | Ser | Ala | Ser | Arg | Phe | Gly | Leu | |
| | | 195 | | | | | 200 | | | | | 205 | | | | |
| CCA | TCT | CTG | GGG | GGT | AGG | CGC | CGG | GCA | ACC | CCT | CGG | AGC | CCA | GGC | GCG | 1871 |
| Pro | Ser | Leu | Gly | Gly | Arg | Arg | Arg | Ala | Thr | Pro | Arg | Ser | Pro | Gly | Ala | |
| | 210 | | | | | 215 | | | | | 220 | | | | | |
| GAC | GTA | CAG | GCG | GCG | GGT | GCG | CTG | ATG | TGG | GGC | GTA | CGC | GCG | GCT | CCA | 1919 |
| Asp | Val | Gln | Ala | Ala | Gly | Ala | Leu | Met | Trp | Gly | Val | Arg | Ala | Ala | Pro | |
| 225 | | | | | 230 | | | | | 235 | | | | | 240 | |
| GGG | GCG | CGG | GTC | GCA | GCG | GGA | GCT | GAA | ACG | AGC | GGT | CCG | GAC | GAC | GCC | 1967 |
| Gly | Ala | Arg | Val | Ala | Ala | Gly | Ala | Glu | Thr | Ser | Gly | Pro | Asp | Asp | Ala | |
| | | | | 245 | | | | | 250 | | | | | 255 | | |
| GAG | GTG | CCC | TGC | TTG | TTG | GGC | ATC | TCA | GCA | GAG | ACA | CTG | GTG | CTG | GTG | 2015 |
| Glu | Val | Pro | Cys | Leu | Leu | Gly | Ile | Ser | Ala | Glu | Thr | Leu | Val | Leu | Val | |
| | | | | 260 | | | | | 265 | | | | | 270 | | |
| GCA | CCT | CGC | GAC | GGC | CGC | GTG | GTC | TTC | AAT | TGT | GCC | TGT | CGC | GAC | GTA | 2063 |
| Ala | Pro | Arg | Asp | Gly | Arg | Val | Val | Phe | Asn | Cys | Ala | Cys | Arg | Asp | Val | |
| | | 275 | | | | | 280 | | | | | 285 | | | | |
| TTG | GCC | TGG | ACC | TTC | TCA | GAG | CAC | CAA | CTC | GAT | CTG | TAC | CAC | GGG | CGC | 2111 |
| Leu | Ala | Trp | Thr | Phe | Ser | Glu | His | Gln | Leu | Asp | Leu | Tyr | His | Gly | Arg | |
| | 290 | | | | | 295 | | | | | 300 | | | | | |
| GGG | GAG | GCG | ATC | ACG | CTG | CGG | CTC | GAC | GGG | GCC | CCA | GGG | CAA | GCC | GTG | 2159 |
| Gly | Glu | Ala | Ile | Thr | Leu | Arg | Leu | Asp | Gly | Ala | Pro | Gly | Gln | Ala | Val | |
| 305 | | | | | 310 | | | | | 315 | | | | | 320 | |
| GGC | GAA | GTC | GTG | GCA | CGT | CTG | CAG | CTG | GTG | AGC | CGC | GGG | TGT | GAG | ACC | 2207 |
| Gly | Glu | Val | Val | Ala | Arg | Leu | Gln | Leu | Val | Ser | Arg | Gly | Cys | Glu | Thr | |
| | | | | 325 | | | | | 330 | | | | | 335 | | |
| AGA | GAA | CTA | GCG | CTG | CCC | AGA | GAT | GGC | CAA | GGT | CGC | CTG | GGC | TTC | GAG | 2255 |
| Arg | Glu | Leu | Ala | Leu | Pro | Arg | Asp | Gly | Gln | Gly | Arg | Leu | Gly | Phe | Glu | |
| | | | 340 | | | | | 345 | | | | | 350 | | | |
| GTG | GAT | GCA | GAA | GGC | TTC | ATC | ACG | CAC | GTG | GAG | CGC | TTC | ACG | TTT | GCG | 2303 |
| Val | Asp | Ala | Glu | Gly | Phe | Ile | Thr | His | Val | Glu | Arg | Phe | Thr | Phe | Ala | |
| | | | 355 | | | | | 360 | | | | | 365 | | | |
| GAG | ACC | ACG | GGG | CTT | CGG | CCT | GGA | GCT | CGT | TTG | CTG | CGA | GTC | TGC | GGC | 2351 |
| Glu | Thr | Thr | Gly | Leu | Arg | Pro | Gly | Ala | Arg | Leu | Leu | Arg | Val | Cys | Gly | |
| | 370 | | | | | 375 | | | | | 380 | | | | | |
| CAG | ACG | CTG | CCC | AAG | CTG | GGT | CCC | GAA | GCT | GCT | GCC | CAG | ATG | CTG | CGC | 2399 |
| Gln | Thr | Leu | Pro | Lys | Leu | Gly | Pro | Glu | Ala | Ala | Ala | Gln | Met | Leu | Arg | |
| 385 | | | | | 390 | | | | | 395 | | | | | 400 | |
| TCT | GCG | CCG | AAG | GTC | TGC | GTC | ACG | GTC | CTA | CCC | CCA | GAC | GAG | AGC | GGC | 2447 |
| Ser | Ala | Pro | Lys | Val | Cys | Val | Thr | Val | Leu | Pro | Pro | Asp | Glu | Ser | Gly | |
| | | | | 405 | | | | | 410 | | | | | 415 | | |
| CGG | CCG | CAG | AGG | AGC | TTT | TCG | GAG | CTC | TAT | ATG | CTC | TCT | CTG | AAG | GAA | 2495 |
| Arg | Pro | Gln | Arg | Ser | Phe | Ser | Glu | Leu | Tyr | Met | Leu | Ser | Leu | Lys | Glu | |
| | | | 420 | | | | | 425 | | | | | 430 | | | |
| CCC | AGC | CGG | CGG | GGG | GGC | CCA | GAG | CCA | GTA | CAG | GAT | GAA | ACT | GGG | AAG | 2543 |
| Pro | Ser | Arg | Arg | Gly | Gly | Pro | Glu | Pro | Val | Gln | Asp | Glu | Thr | Gly | Lys | |
| | | 435 | | | | | 440 | | | | | 445 | | | | |
| TTG | GTC | ATA | TTG | CCT | CCC | ACC | AAG | CAG | CTG | CTA | CAT | TTT | TGC | CTG | AAA | 2591 |
| Leu | Val | Ile | Leu | Pro | Pro | Thr | Lys | Gln | Leu | Leu | His | Phe | Cys | Leu | Lys | |
| | 450 | | | | | 455 | | | | | 460 | | | | | |

-continued

| | | | | | | | | | | | | | | | |
|---|---|---|---|---|---|---|---|---|---|---|---|---|---|---|---|
| GAC | AGC | AGC | AGT | CCT | CCG | GGG | CCT | GGG | GAT | CTG | ACT | GAG | GAG | AGG | ACA | 2639 |
| Asp | Ser | Ser | Ser | Pro | Pro | Gly | Pro | Gly | Asp | Leu | Thr | Glu | Glu | Arg | Thr |
| 465 | | | | 470 | | | | | 475 | | | | | | 480 |
| GAG | TTC | CTG | CGC | AGC | CAC | AAC | TCC | CTG | TCA | TCT | GGA | AGC | TCC | CTG | TCC | 2687 |
| Glu | Phe | Leu | Arg | Ser | His | Asn | Ser | Leu | Ser | Ser | Gly | Ser | Ser | Leu | Ser |
| | | | | 485 | | | | | 490 | | | | | 495 | |
| GAT | GAG | GCT | CCA | GTC | CTG | CCC | AAC | ACC | ACT | CCA | GAC | CTC | CTC | CTT | GTC | 2735 |
| Asp | Glu | Ala | Pro | Val | Leu | Pro | Asn | Thr | Thr | Pro | Asp | Leu | Leu | Leu | Val |
| | | | 500 | | | | | 505 | | | | | 510 | | |
| ACC | ACT | GCC | AAC | CCA | TCT | GCA | CCT | GGT | ACT | GAC | AGA | GAA | ACA | CCC | CCT | 2783 |
| Thr | Thr | Ala | Asn | Pro | Ser | Ala | Pro | Gly | Thr | Asp | Arg | Glu | Thr | Pro | Pro |
| | | 515 | | | | 520 | | | | | 525 | | | | |
| TCC | CAG | GAC | CAG | TCA | GGA | AGC | CCC | AGT | AGC | CAT | GAA | GAC | ACC | AGT | GAC | 2831 |
| Ser | Gln | Asp | Gln | Ser | Gly | Ser | Pro | Ser | Ser | His | Glu | Asp | Thr | Ser | Asp |
| | 530 | | | | | 535 | | | | | 540 | | | | |
| TCA | GGC | CCA | GAA | CTG | AGG | GCC | TCC | ATC | CTG | CCC | AGA | ACC | TTG | TCT | CTG | 2879 |
| Ser | Gly | Pro | Glu | Leu | Arg | Ala | Ser | Ile | Leu | Pro | Arg | Thr | Leu | Ser | Leu |
| 545 | | | | | 550 | | | | | 555 | | | | | 560 |
| CGG | AAT | TCC | ATC | AGT | AAG | ATT | ATG | TCG | GAA | GCT | GGC | AGT | GAG | ACC | CTG | 2927 |
| Arg | Asn | Ser | Ile | Ser | Lys | Ile | Met | Ser | Glu | Ala | Gly | Ser | Glu | Thr | Leu |
| | | | | 565 | | | | | 570 | | | | | 575 | |
| GAG | GAT | GAG | TGG | CAG | TCC | ATC | TCA | GAG | ATC | GCC | TCC | ACT | TGC | AAC | ACA | 2975 |
| Glu | Asp | Glu | Trp | Gln | Ser | Ile | Ser | Glu | Ile | Ala | Ser | Thr | Cys | Asn | Thr |
| | | | 580 | | | | | 585 | | | | | 590 | | |
| ATT | CTG | GAG | TCA | CTG | TCC | CGG | GAG | GGA | CAA | CCC | ATC | TCA | GAG | AGC | GGA | 3023 |
| Ile | Leu | Glu | Ser | Leu | Ser | Arg | Glu | Gly | Gln | Pro | Ile | Ser | Glu | Ser | Gly |
| | | 595 | | | | | 600 | | | | | 605 | | | |
| GAC | CCC | AAG | GAA | GCT | TTA | AAG | TGT | GAT | TCT | GAG | CCA | GAA | CCC | GGG | AGC | 3071 |
| Asp | Pro | Lys | Glu | Ala | Leu | Lys | Cys | Asp | Ser | Glu | Pro | Glu | Pro | Gly | Ser |
| | 610 | | | | | 615 | | | | | 620 | | | | |
| CTG | TCA | GAA | AAG | GTC | TCT | CAC | CTA | GAG | TCC | ATG | CTC | TGG | AAG | CTC | CAG | 3119 |
| Leu | Ser | Glu | Lys | Val | Ser | His | Leu | Glu | Ser | Met | Leu | Trp | Lys | Leu | Gln |
| 625 | | | | | 630 | | | | | 635 | | | | | 640 |
| GAG | GAC | CTG | CAG | AGG | GAG | AAG | GCG | GAC | AGG | GCA | GCC | TTG | GAG | GAG | GAG | 3167 |
| Glu | Asp | Leu | Gln | Arg | Glu | Lys | Ala | Asp | Arg | Ala | Ala | Leu | Glu | Glu | Glu |
| | | | | 645 | | | | | 650 | | | | | 655 | |
| GTT | CGG | AGC | CTC | AGA | CAC | AAC | AAC | CAG | AGG | CTG | CTG | GCA | GAG | TCC | GAG | 3215 |
| Val | Arg | Ser | Leu | Arg | His | Asn | Asn | Gln | Arg | Leu | Leu | Ala | Glu | Ser | Glu |
| | | | | 660 | | | | | 665 | | | | | 670 | |
| AGT | GCC | GCC | ACC | CGC | CTG | CTC | CTG | GCC | TCT | AAG | CAT | CTG | GGT | GCA | CCC | 3263 |
| Ser | Ala | Ala | Thr | Arg | Leu | Leu | Leu | Ala | Ser | Lys | His | Leu | Gly | Ala | Pro |
| | | | 675 | | | | | 680 | | | | | 685 | | |
| ACT | ACT | GAC | CTG | GCC | TGAGTTCCAA | TCTGAATCTG | GACCTGCTTG | GAACTGCCTG | | | | | | | 3318 |
| Thr | Thr | Asp | Leu | Ala | | | | | | | | | | | |
| 690 | | | | | | | | | | | | | | | |

| | | | | | |
|---|---|---|---|---|---|
| GCCCCTCAGA | GCAACTGGGT | CATACTAGTG | CCCTTCCTCA | GGACTTCTTC | CCTGCGCTGA | 3378 |
| GGCGCGTCTT | AGCACTGCCC | CCTCTTCCCA | GCCCATTTGG | TGGCTAATGC | CTGTCCCTGT | 3438 |
| TTGTAAATAT | CCTGTAAAGA | AAAGGAGACA | TCAGAGTTTA | AAAAAAAGAA | ACAACAAGAA | 3498 |
| GAAGCAAAAA | AAAAAAAAAA | A | | | | 3519 |

( 2 ) INFORMATION FOR SEQ ID NO:2:

( i ) SEQUENCE CHARACTERISTICS:
        ( A ) LENGTH: 693 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Tyr  Asn  Asn  Gln  Glu  Ala  Gly  Ala  Ala  Phe  Met  Gln  Phe  Leu  Thr
 1              5                        10                       15

Leu  Leu  Gly  Asp  Val  Val  Arg  Leu  Lys  Gly  Phe  Glu  Ser  Tyr  Arg  Ala
              20                   25                        30

Gln  Leu  Asp  Thr  Lys  Thr  Asp  Ser  Thr  Gly  Thr  His  Ser  Leu  Tyr  Thr
              35                   40                        45

Thr  Tyr  Gln  Asp  His  Glu  Ile  Met  Phe  His  Val  Ser  Thr  Met  Leu  Pro
 50                        55                        60

Tyr  Thr  Pro  Asn  Asn  Gln  Gln  Gln  Leu  Leu  Arg  Lys  Arg  His  Ile  Gly
 65                        70                   75                        80

Asn  Asp  Ile  Val  Thr  Ile  Val  Phe  Gln  Glu  Pro  Gly  Ser  Lys  Pro  Phe
                   85                   90                             95

Cys  Pro  Thr  Thr  Ile  Arg  Ser  His  Phe  Gln  His  Val  Phe  Leu  Val  Val
              100                  105                       110

Arg  Ala  His  Ala  Pro  Cys  Thr  Pro  His  Thr  Ser  Tyr  Arg  Val  Ala  Val
              115                  120                       125

Ser  Arg  Thr  Gln  Asp  Thr  Pro  Ala  Phe  Gly  Pro  Ala  Leu  Pro  Glu  Gly
         130                  135                       140

Gly  Gly  Pro  Phe  Ala  Ala  Asn  Ala  Asp  Phe  Arg  Ala  Phe  Leu  Leu  Ala
145                       150                  155                       160

Lys  Ala  Leu  Asn  Gly  Glu  Gln  Ala  Ala  Gly  His  Ala  Arg  Gln  Phe  His
                   165                  170                       175

Ala  Met  Ala  Thr  Arg  Thr  Arg  Gln  Gln  Tyr  Leu  Gln  Asp  Leu  Ala  Thr
              180                  185                       190

Asn  Glu  Val  Thr  Thr  Thr  Ser  Leu  Asp  Ser  Ala  Ser  Arg  Phe  Gly  Leu
         195                  200                       205

Pro  Ser  Leu  Gly  Gly  Arg  Arg  Arg  Ala  Thr  Pro  Arg  Ser  Pro  Gly  Ala
    210                   215                       220

Asp  Val  Gln  Ala  Ala  Gly  Ala  Leu  Met  Trp  Gly  Val  Arg  Ala  Ala  Pro
225                       230                  235                       240

Gly  Ala  Arg  Val  Ala  Ala  Gly  Ala  Glu  Thr  Ser  Gly  Pro  Asp  Asp  Ala
                   245                  250                       255

Glu  Val  Pro  Cys  Leu  Leu  Gly  Ile  Ser  Ala  Glu  Thr  Leu  Val  Leu  Val
              260                  265                       270

Ala  Pro  Arg  Asp  Gly  Arg  Val  Val  Phe  Asn  Cys  Ala  Cys  Arg  Asp  Val
         275                  280                       285

Leu  Ala  Trp  Thr  Phe  Ser  Glu  His  Gln  Leu  Asp  Leu  Tyr  His  Gly  Arg
    290                  295                       300

Gly  Glu  Ala  Ile  Thr  Leu  Arg  Leu  Asp  Gly  Ala  Pro  Gly  Gln  Ala  Val
305                       310                  315                       320

Gly  Glu  Val  Val  Ala  Arg  Leu  Gln  Leu  Val  Ser  Arg  Gly  Cys  Glu  Thr
                   325                  330                       335

Arg  Glu  Leu  Ala  Leu  Pro  Arg  Asp  Gly  Gln  Gly  Arg  Leu  Gly  Phe  Glu
              340                  345                       350

Val  Asp  Ala  Glu  Gly  Phe  Ile  Thr  His  Val  Glu  Arg  Phe  Thr  Phe  Ala
         355                  360                       365

Glu  Thr  Thr  Gly  Leu  Arg  Pro  Gly  Ala  Arg  Leu  Leu  Arg  Val  Cys  Gly
    370                  375                       380

Gln  Thr  Leu  Pro  Lys  Leu  Gly  Pro  Glu  Ala  Ala  Gln  Met  Leu  Arg
385                       390                  395                       400

Ser  Ala  Pro  Lys  Val  Cys  Val  Thr  Val  Leu  Pro  Pro  Asp  Glu  Ser  Gly
                   405                  410                       415

Arg  Pro  Gln  Arg  Ser  Phe  Ser  Glu  Leu  Tyr  Met  Leu  Ser  Leu  Lys  Glu
              420                  425                       430
```

```
Pro  Ser  Arg  Arg  Gly  Gly  Pro  Glu  Pro  Val  Gln  Asp  Glu  Thr  Gly  Lys
          435                      440                     445

Leu  Val  Ile  Leu  Pro  Pro  Thr  Lys  Gln  Leu  Leu  His  Phe  Cys  Leu  Lys
     450                      455                     460

Asp  Ser  Ser  Ser  Pro  Pro  Gly  Pro  Gly  Asp  Leu  Thr  Glu  Glu  Arg  Thr
465                      470                     475                          480

Glu  Phe  Leu  Arg  Ser  His  Asn  Ser  Leu  Ser  Gly  Ser  Ser  Leu  Ser
                    485                      490                     495

Asp  Glu  Ala  Pro  Val  Leu  Pro  Asn  Thr  Thr  Pro  Asp  Leu  Leu  Leu  Val
               500                      505                     510

Thr  Thr  Ala  Asn  Pro  Ser  Ala  Pro  Gly  Thr  Asp  Arg  Glu  Thr  Pro  Pro
          515                      520                     525

Ser  Gln  Asp  Gln  Ser  Gly  Ser  Pro  Ser  Ser  His  Glu  Asp  Thr  Ser  Asp
     530                      535                     540

Ser  Gly  Pro  Glu  Leu  Arg  Ala  Ser  Ile  Leu  Pro  Arg  Thr  Leu  Ser  Leu
545                      550                     555                          560

Arg  Asn  Ser  Ile  Ser  Lys  Ile  Met  Ser  Glu  Ala  Gly  Ser  Glu  Thr  Leu
                    565                      570                     575

Glu  Asp  Glu  Trp  Gln  Ser  Ile  Ser  Glu  Ile  Ala  Ser  Thr  Cys  Asn  Thr
               580                      585                     590

Ile  Leu  Glu  Ser  Leu  Ser  Arg  Glu  Gly  Gln  Pro  Ile  Ser  Glu  Ser  Gly
          595                      600                     605

Asp  Pro  Lys  Glu  Ala  Leu  Lys  Cys  Asp  Ser  Glu  Pro  Glu  Pro  Gly  Ser
     610                      615                     620

Leu  Ser  Glu  Lys  Val  Ser  His  Leu  Glu  Ser  Met  Leu  Trp  Lys  Leu  Gln
625                      630                     635                          640

Glu  Asp  Leu  Gln  Arg  Glu  Lys  Ala  Asp  Arg  Ala  Ala  Leu  Glu  Glu  Glu
               645                      650                     655

Val  Arg  Ser  Leu  Arg  His  Asn  Asn  Gln  Arg  Leu  Leu  Ala  Glu  Ser  Glu
               660                      665                     670

Ser  Ala  Ala  Thr  Arg  Leu  Leu  Leu  Ala  Ser  Lys  His  Leu  Gly  Ala  Pro
          675                      680                     685

Thr  Thr  Asp  Leu  Ala
690
```

( 2 ) INFORMATION FOR SEQ ID NO:3:

( i ) SEQUENCE CHARACTERISTICS:
( A ) LENGTH: 5687 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:3:

```
GGATCCCAAA  CTGAGGCAGC  AGCCTCCTAG  CCAGGCCCTA  AGAGCCAAAC  CCATGGGCTG     60
GTCCCTCATT  GGAGCCCATG  GCCAGGACTG  ACTTTGCCTC  TGGGGCCTGC  ACTGCCCCCA    120
AGGCTGGCCT  CCTTAGCCTG  GACCTGGGGC  CCGATATGTG  GCAAGGGTGG  GTTCATTCGT    180
TCTTTTGTCA  TTTTTCTTTC  TTTTTTTTC   TGTGCTTCAG  AGACACCAAA  TTAATAACAC    240
TATTTTTGAT  TTGGTTGGC   AGTTTTATTT  TCTGTGGGAC  GAGGTGAGGT  TGGTAGAGGT    300
GCCGGAGGGA  GGCTGAAGTC  AGAAGAGTGT  GAGGGATAAG  GGGTCAGACT  GCTGGGCTCC    360
AGGCAGACAT  GAGGTGGGAT  GGGCTGCCTT  CCTCACCTGC  CTCTGCCTTT  CTTTTTTTT    420
TTTTTTTTTT  AATGGTTTAA  GAGCTTATTA  TAGAAATGCC  AGTCGAGGGA  AGAGAAAAGG    480
```

```
TAGAGAGAGA    GAGTGTGTGG    GACGGGGAAG    GCTAGAGAAG    AAGAAAGAGA    AAGGAGAGAA      540

AAGACAAAGG    GAAGAGGAGA    AAGAAGTGAG    AGGATAAAGG    AGAGAGCTGA    GCCTCTGCTT      600

TTCAAGCAGT    CCTCTATCCC    CAGGTGGCTC    ACACATCCAT    CAGCCTTGAT    CTTATCAAAG      660

ACTGCTCAAC    CTCATTTGTC    CAAGCTTAAG    AAAATAACAG    GTGAATAGAA    AGGATTCTAT      720

TCGTTTTTGA    GACAGGGGCT    TACCATGTAC    TCCCTATGTA    CATCAGGCTG    GCCTTGACCT      780

CAGATCCACC    TGCCTCTGCC    TTCAGAGTGC    TGGATTTAAT    GGTGTTCGCC    ATTGCATAAA      840

TGGTAGCCTG    TGTAGATCAG    TTATCTAGCT    TGGCCCAGCC    CTTAAAGAGT    GAAATAGTTT      900

CTGGCCCTAA    TACCTGCTGT    CTGCTGAGCC    ACAGCAGGAC    ACTAAGTGGC    CTCTAGCGCT      960

CCAATTGGTC    TGGAAGGCAG    GTACATTTGT    TCCCATTTCT    CGGTGAAGTC    ACTGACTGGG     1020

CTAGGACCGG    GAGTTAAAAG    AGCAGCTGAA    GGCTGGGACA    GAGAACTTCA    GGCTGTCCGG     1080

GGCTGCCTAG    GTTCCTGTCG    GAGGTCCCCA    CCCACTGTGC    TTCCGCCTTA    GACAGCTCCC     1140

GGGTAGTCCC    GCCCCTCCAC    TACGTACCGC    CTCCATCCTG    GCCCGCCCC     CAGGGAGGGA     1200

GGCGCCGGGA    GCGGTGTGAG    CAGGCAGCGG    GACCTTGGTG    CGGAAGGCAG    CGGTGGCCAG     1260

CTTGAGCCCG    AGAGGTACTG    GCGGGATCAG    GGATCGGGAG    GCACCAGGTT    CGGGCTGGAT     1320

ACCCAACAAA    GTAGCCTGGA    CGTGAACCCT    GTAGTGTGGG    GAGGAACGGG    ACTATTGGCT     1380

GCTTTCGCTA    CACGCACCCC    ACCCAACCTC    CTGCCCCAGT    CCAGCCCCGA    GTCAGCACGT     1440

CCAGTGTTCT    GCTCCTGCTG    GCAGCTCCCA    CTCCCTCCTC    TGCATGAGCA    GATTCAGAGC     1500

TCACTGAGTG    GATTCATTGG    TTCTGGACTT    TTCTCAGCAA    TGCTGGCGCA    GCTGCTCCTG     1560

CTGCTGTTGT    TGTTGTGGGG    CTCCCCCTAT    TCTGGGGCTC    CCCTGTTCCC    AGTGTGACCT     1620

CTTTCCCAGC    CTTTGCAATC    CTGAGTCTGG    CCTGGGAGGA    AACATCTGCA    GCACTCCCTG     1680

GCAACAGAAA    TAGGGTCACG    ACCTCCAGAT    GTGCTGGGAA    GCATCCAGCG    CCTCCTCCTG     1740

GGGCAGCCAG    GCCTTCCGGA    TCTGTGGGGG    CGGGCCCCCC    CTTTCCCCCC    CTCAGTGACA     1800

CAGGCTGCAA    GGAATGTCTG    GGCCTCAATG    GACCTTGTGT    AAGATGAGGG    GTGGGGGGCA     1860

GAGCAAGTAC    ACACCTTAAG    GCAGGGCCAG    AACAAGAGGG    AGCTCCTGGA    CTGGGCTGCA     1920

CACATTCCCA    GGGCTCCTCC    CGGCACTGCG    GCCTCAGTCT    GTGCCCACGC    TTGGTCTATG     1980

GACCTGGGCG    CCTGCACAGT    TCACACACGG    ACATAGTTGG    CCTTCACCTT    TCAGTTTCCA     2040

AGGAGTCTTC    AAAGAACTCA    TGAAGAGTTC    CAGACTCAGA    GAGCTTATCC    TAGAAGACAG     2100

ACAGACAGAC    AGGAAGACCC    TGAGGAGGTC    TGCTCTTATT    TAATTCTGGA    GACCCAGCTG     2160

AGGGGCACCG    TGGAGCTGCT    CCCTGTCCCC    TCCCAGCCTG    GCCCCCTTGA    TGCCACTGGA     2220

TGATGCAAAA    AAAAGTACTA    ATGGAGGCCT    GCCCCTGCCC    CAGCTGTTGG    CTCCATTCCT     2280

ACGTCACGCC    GAGGTAGGCT    CGGCCTTCTC    ACACCTTTTG    CACCTGCCTA    GTGTAGCTTC     2340

ACCACATTTC    CGCACTTAGT    AGGTCCCTGG    GGCCTTGGGT    GTTTCAGCCT    TACATCCTGT     2400

GAGACCTTGA    GCCTCTCCCA    TCTCCCCTCA    CAAGGCTGCC    TTACTCCTAC    GCACACGGGC     2460

AGAGTAGGCA    GGTGCAGCTC    TGACAAGTCC    AGAAGCAGCA    GTCTCAACCT    GTGTGCTGGG     2520

ACCCCTTTGA    GGGTCGAGCA    GTCCTTCACA    GGGGTCACAC    TTGAGATATT    TATCTTCTTC     2580

TTCTTCTTCT    TTTTGTTTTT    CAAGACAGGG    TTTCTCTGTG    TAGCCCTGGC    TATCCTGGAA     2640

CTCACTCTGT    AGACCAGGCT    GGCCTTGAAC    TCGAAATCTG    CCTGCCTCTG    ATTCCCCAGT     2700

GCTAGGATTA    AAGGAGTGTG    CCAACACTGC    CCGGCTCATG    TTATGATCTT    AAGGGCAGCA     2760

AAATTACAGT    GGTGAAGTAG    CAATGAAAAT    AATTTTCTGG    CTGTGAGGTC    ACCACCGCAT     2820

TAGGGAAACT    GTATTAAAGC    GTCACAGAGT    TAAGAAGGTT    GAGAACTACT    GCCTTCGAGA     2880
```

-continued

```
TTCAGAGACA  AGGTTCAAAT  TCTAGTTTGA  ACATGGAACT  AATTCAGGCA  AGCTCATCTT  2940
CTTAACTGGG  CCTCACTGTG  ACCTGTCTCA  CTGGGTTCAG  ACCTCCCTGT  CCATGCATGT  3000
GAGGCCAGGT  AAACAGACAT  CCACAGGGTC  CTGATTGGGA  TTAGCCTCTC  TCACCCCTGG  3060
GAGTGGGCAT  CGTGACCTGC  AAGAGATTAG  TATTAGTCTT  GTCCTTTAGA  CTTAGGTGTC  3120
TTGGGTCCCA  TGACTGAGCT  GTTGTGACCC  TAGCACCTTC  CTCAGGATAT  AGGAGCCAAG  3180
CAGGGGGCTG  GGCTGAGTTG  GGGCCACTTC  CTGTGTTATA  GGAAGTCCTC  TCACCACTGC  3240
TTCTGTCCTG  CATGCAGCTG  CCCCAGGAGC  TCCTGTGTCC  TTGAGGTATT  GAGACTGCGG  3300
GAATTGAGGG  CACTGAGTCT  AGGCCTTGGG  TGCTCAGTCT  CTTTGGGGAC  TCTGGAGGAA  3360
GTGGGAGGTA  CCAGGGAGGA  AGGTCTCTGG  GGACGGACGT  CTCCCTTTGT  ACAAGTGGGC  3420
AAGACTCAGA  CACCAGTGAC  TGCTTTGATT  TCCGTTCTGG  TGAAAACTGT  TCAGAATTTG  3480
GTGGCAACCC  TCACTTTGAG  CCTAGTTCCA  CAGCCAAGGT  GTACAGGGA   GAACTGGGAG  3540
GGGCCGGTGC  CACTAGACCC  AGTCACTAGC  ACCCCGAGAG  CAAAGCATCC  CAGTTCAGCT  3600
CCCAGCCTTG  ACCTAAGCCT  GGGATGGGGC  TGGAAACTTC  AGCCCAGGCA  GACAAGGAAG  3660
TGGCCAGGAA  AGCGGAAGCA  GCTTTGATGG  TCCGGAGGGG  GCCGGAAGCT  AAATGGGGTG  3720
GTGGAAGACT  GGGCTGGGGG  CCTGAGTTCC  TGTTTTCTCC  CCAGGCCCAT  CTGAACAGCC  3780
CCCTCCTCTG  CAGTGCAGGA  ACCTCTGAAC  GCTCAGCCTT  CTGGCTGGGC  ACCAAGGACC  3840
CGTGCCCACC  AATGCGGCCC  GGCCCCAGA   GAGTCAGGCC  CACAGGAGCA  CGCCCATGTG  3900
GGCCGGCGGT  GTGGGGAGCC  CTCGGCGGGT  GCATGGCCTG  CACCTACCGA  TGACCTCTTT  3960
GCCCGTAGCT  TCGCCAACCT  GCCCGGCCCC  CACTGACACC  ACATACCTTT  GAGCCGAGGC  4020
CAGCTCGGGC  CACTCTTGCG  CAGTGGCAGT  GATGCTGGTG  AAGTCGGCCC  CCTACACCAG  4080
CCAGCCCCCG  TGCCGTGCC   CACAGCCACG  AGGATGCCAG  CCGCCCTGCT  GCAACCCCTA  4140
CTCGGCTCTT  CACTGACCCA  CTGGCACTGC  TAGGGTTGCC  AGCAGAAGAG  CCAGAGCCCA  4200
GGTTCCGCC   AGTGCTGGAA  CCCCGGTGGT  TTGCTCACTA  TGATGTGCAG  AGCTTGCTCT  4260
TTGACTGGGC  TCCACGACCT  CGGGGGACAG  GCAGCCATAC  AGAGGCAAAC  TCTGGGACCT  4320
TAGCTGAGGG  CCAGACTACC  ACCTCAGATC  TACTGCTCGG  GGCACCTGGC  TTTGTGAGCG  4380
AGCTTGGTGG  TGAGGGTGAG  CTAGGGCTGG  GTGGGCCAAT  ATCCCCACCT  GTGCCCCCTG  4440
CACTGCCTAA  TGCGGCTGTG  TCCGTCCTGG  AGGAGCCACA  GACCCGGACC  ACACTTACAG  4500
CCTGGAGCAC  GCAGATCTGG  GTGCAGGCTA  CTACCGCAAG  TACTTCTATG  CAAAGGTAA   4560
GGGGCAGGCG  AGCCTGGGAG  AGGCAGGAGA  GGATCTGGGT  CGGAGGTCCC  TGTGGTCTTC  4620
TACATTCTAT  CAGTGGGAGG  CTCATGGGCT  GGCCTTCCCT  GTAAAAAGG   GGCAGGAGCT  4680
GAATTGGGCT  CTGTTGGCTC  AACTCTGACC  ACCTCTTTAA  GGCCAAGAAT  GGTGTCACAC  4740
CTGAAGTCAG  GGAGTGCACT  TACCTCTGAG  GCTCATCTTC  ATAACCTCCA  GGAGGCCAGT  4800
GAGCGATTTC  CTATTTCCAT  ATCTGTGTGA  TGAAACCCTG  TTCTCATCAT  TAGCAGGAAA  4860
AGCAGCTTCC  GTGTCTTGAA  TGGAGAACC   TAAGCTTTGG  TGGAGCCAGG  GCAGCATTTA  4920
ACTAGGAGGA  CTTAGGCATT  TGTTCCCCGG  TCCTGGGAAC  AAGGTGTAAC  CGTGGGTGGG  4980
ACTGCAAACT  GGGGTGGAGT  GAACTCCAG   GTTCAGCGCT  TGGTGAGAGA  ATACCTAGGG  5040
TGGTACTTCT  GTGGTGGGAG  TAGTCAAGAA  GGGATAGGGT  GGTCTGTGGG  TTTGACTGAA  5100
AGGCCACCGA  CCGACCAACC  AACGACCCTC  CACCCCACC   CCACAGAAC   ACCAGAACTT  5160
CTTTGGGTTG  GATGAGGCGC  TGGGTCCGGT  GGCCGTGAGC  CTGCGACGGG  AGGAGAAAGA  5220
GGGCAGCGGA  GGGGGCACCT  ACACAGCTAC  CGGGTCATCG  TGCGGACCAC  GCAGGTGGGC  5280
```

-continued

```
TGGGATTACA  GGCTCAGGAG  GCAGGTTTCC  TCCACCACAG  CCTATACAAA  AACTGAATGT    5340

CTCTACATCC  TTAGCTCCGG  ACCCTCCGTG  GCACCATCTC  GGAGGACGCA  CTGCCTCCCG    5400

GCCCCCCGAG  CGTATCTCCG  AGGAAGCTTC  TGGAACATGT  GCTCCACGGC  TGAGCCCACC    5460

TGCCTGCGCC  TGGGTTCAGC  CTCTCCCAAG  GTGCCCCGCA  GCTGCTTACT  CTGGATGAGC    5520

AAGTGGTGAG  TGGCTGGGAG  GTAAGGAGGG  AGTGCAGCAT  CCCGGGGAAG  ATGGGGCTGA    5580

CCTTCATCTC  CCTAACTAGC  TAGCTTCCCG  CTCCCTAACC  CTGACCTGAT  CTGACGGACC    5640

TCAAGGTACA  GCTGATCCAC  CTCCAAGCCT  TTCGAGAGA   AGGATCC                   5687
```

(2) INFORMATION FOR SEQ ID NO:4:

(i) SEQUENCE CHARACTERISTICS:
        (A) LENGTH: 6645 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(904..1015, 1356..1459, 1726..1883, 2009
            ..2618, 2890..3164, 4291..4509, 4598..4709, 4795
            ..4903, 5017..5117, 5200..5255, 5447..5525, 5598
            ..5741)

(xi) SEQUENCE DESCRIPTION: SEQ ID NO:4:

```
GGATCCCCAT  TACAGATGGA  TGTGAGCCAC  CATGTGTTGC  TGGGAATTGA  ACTCAGGAAC      60

CTCTGGAAGA  GCAGTCAATG  CTCTTAACCA  CTGAGCCATC  TCTCCAGCTA  ACCTTGTTTC     120

AAACAAACAA  AAAATTGCAG  GTACGTGTCT  AGATTCCAAT  ATTTGGGAGA  TACAGGCAAA     180

TGATCAGGAT  CAGGCAGTCT  TAGCTATATA  TGAGTTTAAG  TACAGCCTGG  CCTATGTACT     240

ATAGCCTATC  AAAAGACAA   ACAGGAAGGG  GACAGAAATG  ACTCCAAACC  TCAGAGGGCT     300

GGGGTGCCAG  CACACTGGAG  CCTTGAGCTG  AGGGGACGG   GAACATGGGC  ACCAGTCTTG     360

GCAGGGATC   TCAGCCTTCC  TAGTGCCCTT  TCCCACAGCT  CCACATGGTG  TGGTGACCCT     420

GATCAAAAAT  TATTTTCATT  GCCACTTCAT  AACTGTAATT  CTGCTACCCT  TAGGAATTGT     480

ACCATAAACA  CCTGACACAC  AGGGTCTCTG  CTGCATGCGA  CCCCTGTGAA  TGGGCCGTTA     540

GACCCTCAGA  AGGGTCACAA  CTATAGGCTG  AGAACCCACT  GGTGTATAGG  GTCCTTTCTG     600

GGAGTTATCT  CTTTTGTTGC  TGGAGAAGTC  ATTAAATCCT  CTGCCTCTTC  CCTGTGACCT     660

CCCTGCTCTC  ACGAGCACAG  GAGAGGGCAG  GTAGAACGCA  CTTGATGGGC  AAAGATGCCC     720

AAATGGCTCA  GAGTTCCTAC  CAGGGCAGCC  CAGCCCCAAA  GGCCAGCTCT  TCCCATTCTC     780

TACAGGGTGG  GCTGCCAGGG  TACTGAAGCC  TTTGTCTTCT  GTTGTCCATG  ACCCCCTCAG     840

CTGAGCTTCC  AACGCAAGGT  GGGCATCCTG  TACTGCCGCG  CAGGCCAGGG  CTCTGAGGAA     900

GAG  ATG  TAC  AAC  AAC  CAG  GAG  GCC  GGA  GCA  GCC  TTT  ATG  CAG  TTC  CTT          948
     Met  Tyr  Asn  Asn  Gln  Glu  Ala  Gly  Ala  Ala  Phe  Met  Gln  Phe  Leu
       1              5                      10                     15

ACT  TTG  CTG  GGT  GAT  GTG  GTG  CGA  CTC  AAA  GGC  TTT  GAA  AGT  TAC  CGG          996
Thr  Leu  Leu  Gly  Asp  Val  Val  Arg  Leu  Lys  Gly  Phe  Glu  Ser  Tyr  Arg
               20                      25                     30

GCC  CAG  CTG  GAT  ACC  AAA  A  GTGAGCGTCC  CCCGCCCCTA  AGGGACTGGA                    1045
Ala  Gln  Leu  Asp  Thr  Lys
               35

GATGCAGGGC  AGAACTTTAT  CAGTGTTCCT  TAGTCTGTGG  TGGCTGGGGC  TGAGAATGGG    1105

GGAGTGCCCT  GCTCCCTCTA  AGTCTTATTT  CTGGATTCGT  TCTATCTCAG  CACCCCTATA    1165
```

```
CTGATTCCCC TTCACCCTGG TGTGGGGCCG TAGTCTATAG GAGAGGGGAG GGAATTTACC      1225

AAGGATGGGG CTCTTGGTCT TCGTGGCCTA AGCAATAGCT GGTGGCTGGG ACATAGAAGT      1285

AAATTTAAGA CTCATTGAAG TCACCCACAC CCCCCATGTT CTCTTTGTGT CCCCAATTGT      1345

CTGGCTACAG  CG GAT TCC ACG GGC ACA CAC TCA CTC TAC ACC ACC TAC         1393
              Thr Asp Ser Thr Gly Thr His Ser Leu Tyr Thr Thr Tyr
               40              45                      50

CAA GAC CAT GAG ATC ATG TTT CAC GTG TCC ACG ATG CTG CCT TAC ACG        1441
Gln Asp His Glu Ile Met Phe His Val Ser Thr Met Leu Pro Tyr Thr
             55                  60                      65

CCT AAT AAC CAG CAA CAG GTGTGTGAGG AGCTGGGCCA GGCCAAAGAC               1489
Pro Asn Asn Gln Gln Gln
             70

TTTCGGGAAG CAGTGGCGGG TGTTACTTGA GTGCTTAATA TCAGAACGGT GGTCTGAGCT      1549

CTGCTGAACC TAACAACACC CACCCCCCA CCCCTTGGCT GTACCACCTT CGCAAATACC       1609

CTCCTCGGGC CTTTATAAGG TGCAGGTGGG GAACCACTGA CACCTTTGCC ATGCCTAAAT      1669

GAGGGACTGG GGGGGGCACA AAGCTCACCT CTCATTTGCC TACCTTTAAC CCCCAG          1725

CTC CTG AGG AAG CGT CAT ATC GGC AAC GAT ATT GTG ACC ATC GTG TTC        1773
Leu Leu Arg Lys Arg His Ile Gly Asn Asp Ile Val Thr Ile Val Phe
             75                  80                      85

CAG GAG CCC GGT AGC AAG CCC TTC TGC CCT ACA ACA ATC CGC TCT CAC        1821
Gln Glu Pro Gly Ser Lys Pro Phe Cys Pro Thr Thr Ile Arg Ser His
 90                  95                     100

TTC CAG CAC GTT TTC TTG GTG GTG CGT GCG CAT GCT CCC TGC ACC CCA        1869
Phe Gln His Val Phe Leu Val Val Arg Ala His Ala Pro Cys Thr Pro
105                 110                     115                 120

CAC ACC TCA TAC AG  GTGGGTGCTA GGGTGAACTC AGGTCATGGG CACCGATGAT        1923
His Thr Ser Tyr Arg
                125

TGACACATTC CTCGCACCGA TGATTGGACA CATTCCTCGC CCCCTTCCGC CCCACGTTCC      1983

CTCACTACAG CCTTCCTCCA CGCAG G GTG GCA GTG AGC CGC ACC CAG GAC          2033
                             Val Ala Val Ser Arg Thr Gln Asp
                                                     130

ACT CCT GCC TTC GGG CCT GCG CTG CCA GAA GGC GGA GGC CCC TTT GCA        2081
Thr Pro Ala Phe Gly Pro Ala Leu Pro Glu Gly Gly Gly Pro Phe Ala
135                 140                     145

GCC AAT GCC GAT TTC CGG GCC TTT CTG TTG GCT AAG GCA CTC AAT GGT        2129
Ala Asn Ala Asp Phe Arg Ala Phe Leu Leu Ala Lys Ala Leu Asn Gly
150                 155                     160                 165

GAG CAA GCG GCT GGT CAT GCA CGC CAG TTC CAC GCC ATG GCT ACA CGC        2177
Glu Gln Ala Ala Gly His Ala Arg Gln Phe His Ala Met Ala Thr Arg
                170                     175                 180

ACA CGC CAA CAG TAC CTG CAG GAC CTG GCT ACT AAT GAA GTG ACC ACT        2225
Thr Arg Gln Gln Tyr Leu Gln Asp Leu Ala Thr Asn Glu Val Thr Thr
                185                     190                 195

ACT TCG CTG GAC TCG GCT TCG CGG TTT GGC CTG CCA TCT CTG GGG GGT        2273
Thr Ser Leu Asp Ser Ala Ser Arg Phe Gly Leu Pro Ser Leu Gly Gly
             200                     205                 210

AGG CGC CGG GCA ACC CCT CGG AGC CCA GGC GCG GAC GTA CAG GCG GCG        2321
Arg Arg Arg Ala Thr Pro Arg Ser Pro Gly Ala Asp Val Gln Ala Ala
215                     220                 225

GGT GCG CTG ATG TGG GGC GTA CGC GCG GCT CCA GGG GCG CGG GTC GCA        2369
Gly Ala Leu Met Trp Gly Val Arg Ala Ala Pro Gly Ala Arg Val Ala
230                     235                 240                 245

GCG GGA GCT GAA ACG AGC GGT CCG GAC GAC GCC GAG GTG CCC TGC TTG        2417
Ala Gly Ala Glu Thr Ser Gly Pro Asp Asp Ala Glu Val Pro Cys Leu
                250                     255                 260
```

-continued

| | | | | | | | | | | | | | | | | |
|---|---|---|---|---|---|---|---|---|---|---|---|---|---|---|---|---|
| TTG | GGC | ATC | TCA | GCA | GAG | ACA | CTG | GTG | CTG | GTG | GCA | CCT | CGC | GAC | GGC | 2465 |
| Leu | Gly | Ile | Ser | Ala | Glu | Thr | Leu | Val | Leu | Val | Ala | Pro | Arg | Asp | Gly | |
| | | | 265 | | | | 270 | | | | | 275 | | | | |

| CGC | GTG | GTC | TTC | AAT | TGT | GCC | TGT | CGC | GAC | GTA | TTG | GCC | TGG | ACC | TTC | 2513 |
|---|---|---|---|---|---|---|---|---|---|---|---|---|---|---|---|---|
| Arg | Val | Val | Phe | Asn | Cys | Ala | Cys | Arg | Asp | Val | Leu | Ala | Trp | Thr | Phe | |
| | | 280 | | | | 285 | | | | | 290 | | | | | |

| TCA | GAG | CAC | CAA | CTC | GAT | CTG | TAC | CAC | GGG | CGC | GGG | GAG | GCG | ATC | ACG | 2561 |
|---|---|---|---|---|---|---|---|---|---|---|---|---|---|---|---|---|
| Ser | Glu | His | Gln | Leu | Asp | Leu | Tyr | His | Gly | Arg | Gly | Glu | Ala | Ile | Thr | |
| | 295 | | | | 300 | | | | 305 | | | | | | | |

| CTG | CGG | CTC | GAC | GGG | GCC | CCA | GGG | CAA | GCC | GTG | GGC | GAA | GTC | GTG | GCA | 2609 |
|---|---|---|---|---|---|---|---|---|---|---|---|---|---|---|---|---|
| Leu | Arg | Leu | Asp | Gly | Ala | Pro | Gly | Gln | Ala | Val | Gly | Glu | Val | Val | Ala | |
| 310 | | | | | 315 | | | | 320 | | | | | 325 | | |

| CGT | CTG | CAG | GTGAGGCAGT | GTCAAAAACT | AAGGTCCCCT | GTCGGGTGC | 2658 |
|---|---|---|---|---|---|---|---|
| Arg | Leu | Gln | | | | | |

| GTATCGGGGG | CGGGGCCTAT | TGGAAACTCC | GTTAGCTGCT | GTGGTGGGGC | GGGGAAAAGG | 2718 |
|---|---|---|---|---|---|---|
| TACTTGCACA | GGTGACTCTC | AGAGTCTCCA | ATTCGAATAC | ACAACTATCA | GGTAGGTCGC | 2778 |
| TAGGGCTCCT | GGGGCATGCC | GGGTTAAATC | GATCGAGGCA | GGGGCGGGAC | CAGGGCGGGG | 2838 |
| CCTCTGTGAA | GCCACGCCCC | AAGGCCACTC | TCACCCAGCC | TTTCCTTGCA | G CTG GTG | 2895 |

|  |  |  |  |  |  |  |  |  |  |  |  |  |  |  |
|---|---|---|---|---|---|---|---|---|---|---|---|---|---|---|
| | | | | | | | | | | | | Leu | Val | |
| | | | | | | | | | | | | | 330 | |

| AGC | CGC | GGG | TGT | GAG | ACC | AGA | GAA | CTA | GCG | CTG | CCC | AGA | GAT | GGC | CAA | 2943 |
|---|---|---|---|---|---|---|---|---|---|---|---|---|---|---|---|---|
| Ser | Arg | Gly | Cys | Glu | Thr | Arg | Glu | Leu | Ala | Leu | Pro | Arg | Asp | Gly | Gln | |
| | | | | 335 | | | | | 340 | | | | | 345 | | |

| GGT | CGC | CTG | GGC | TTC | GAG | GTG | GAT | GCA | GAA | GGC | TTC | ATC | ACG | CAC | GTG | 2991 |
|---|---|---|---|---|---|---|---|---|---|---|---|---|---|---|---|---|
| Gly | Arg | Leu | Gly | Phe | Glu | Val | Asp | Ala | Glu | Gly | Phe | Ile | Thr | His | Val | |
| | | 350 | | | | 355 | | | | | 360 | | | | | |

| GAG | CGC | TTC | ACG | TTT | GCG | GAG | ACC | ACG | GGG | CTT | CGG | CCT | GGA | GCT | CGT | 3039 |
|---|---|---|---|---|---|---|---|---|---|---|---|---|---|---|---|---|
| Glu | Arg | Phe | Thr | Phe | Ala | Glu | Thr | Thr | Gly | Leu | Arg | Pro | Gly | Ala | Arg | |
| | 365 | | | | 370 | | | | | 375 | | | | | | |

| TTG | CTG | CGA | GTC | TGC | GGC | CAG | ACG | CTG | CCC | AAG | CTG | GGT | CCC | GAA | GCT | 3087 |
|---|---|---|---|---|---|---|---|---|---|---|---|---|---|---|---|---|
| Leu | Leu | Arg | Val | Cys | Gly | Gln | Thr | Leu | Pro | Lys | Leu | Gly | Pro | Glu | Ala | |
| | | 380 | | | | 385 | | | | | 390 | | | | | |

| GCT | GCC | CAG | ATG | CTG | CGC | TCT | GCG | CCG | AAG | GTC | TGC | GTC | ACG | GTC | CTA | 3135 |
|---|---|---|---|---|---|---|---|---|---|---|---|---|---|---|---|---|
| Ala | Ala | Gln | Met | Leu | Arg | Ser | Ala | Pro | Lys | Val | Cys | Val | Thr | Val | Leu | |
| 395 | | | | 400 | | | | | 405 | | | | | 410 | | |

| CCC | CCA | GAC | GAG | AGC | GGC | CGG | CCG | CAG | AG | GTCAGGGCAC | CGGGTGGGGG | 3184 |
|---|---|---|---|---|---|---|---|---|---|---|---|---|
| Pro | Pro | Asp | Glu | Ser | Gly | Arg | Pro | Gln | Arg | | | |
| | | | | 415 | | | | | 420 | | | |

| TTGTGGGGGG | TGGGTAGGAG | GACTCAGCGG | CTGGCCCATT | CTGTGCCTCC | CGTGTTAGCA | 3244 |
|---|---|---|---|---|---|---|
| TCAGCATGCT | CTGAATCGTA | CGGTATTCAT | CTAGACTTGA | AACTGTTTAA | GCTCGTGCTT | 3304 |
| TCCCTCTCTA | AAGGTTAAAT | AGCTCCTTCT | ATTATTTCAA | TGTATTAGCT | CCTCCACACC | 3364 |
| AAGTACACAC | TAATTGACCA | CTTCCTATTC | TAAACCCAAT | ATAGGCAAAC | TTTCCCCATA | 3424 |
| GAACCCCTAA | TAGTAAATAC | TTTTAGACTT | TTGGAGCCAC | TATTCTTGCC | ACAGTCACTC | 3484 |
| GACTCTTTTG | TAGGAAAATG | AATGTGTGCC | AGCATCTACT | AAAACTATGA | CTGGAATTTT | 3544 |
| AGGATTTGAT | TTGGAGCTCC | TTGTCTTGTG | AAGGGGTAAA | CCCAATGTAA | GGTCAAAAAA | 3604 |
| AAAAAAAAAT | CCAAGTAGAA | ACACATTATG | CTCAGACTGT | GTAATTTTTA | CATGCCATGA | 3664 |
| AGTACTCTAT | TAATACCTTT | TAAATTATTT | AAACATCTAA | GAACTAAGGC | CAGAGAAGTG | 3724 |
| GCTCAGCCAT | TAAGAGCATT | TGCTGCTCTT | GCAGAGGACC | TGAGTTGGAT | TCCTAGCACC | 3784 |
| CACACAGTGC | TCTGTGACAG | CCTGTATGTA | ACTTCAGATC | CAGGGGTCTC | ACACCCTCTT | 3844 |
| CTGGTCTCCA | CAGGTGTTGC | ATTCACATGT | GCCTGCTCCC | TCCCACGTA | AATACACATA | 3904 |
| TACACATCAA | TAAATAGTTC | AAGATCTCTA | AAAACTATTC | TTAGCAGATA | GGAGTTTCAA | 3964 |

| | |
|---|---:|
| AGACTGGCAT GTGTGCTAAT AAAAAACAAA GAGAAGCATG GGCTGGATGG CTCCAGGCAG | 4024 |
| TGCACTGTGG ATGCTAAGCG ATTTATATTA CATTGTTTCC ACTGTAAATA CTCTTATGTA | 4084 |
| TGTTTGACAG AAAACAGAGA GAGTGGCCTG CTTAGGAGAC ATGGGCAGCC ATGGATACAA | 4144 |
| AGTTAACAGT GATATTTGTC TGCTGTAGAG TCAGGATGCC TGGAGCTCTC TTCCTTTTGG | 4204 |
| ATGTCTCTGG CAGTGGCTGG GATGGGGTGG ATGCTGTGGA GGGGATGGAG GGTCCTACCT | 4264 |

```
GATGCTGCCC CACCCCCACC CTCCAG G AGC TTT TCG GAG CTC TAT ATG CTC      4315
                                Ser Phe Ser Glu Leu Tyr Met Leu
                                                            425

TCT CTG AAG GAA CCC AGC CGG CGG GGG GGC CCA GAG CCA GTA CAG GAT     4363
Ser Leu Lys Glu Pro Ser Arg Arg Gly Gly Pro Glu Pro Val Gln Asp
    430             435                 440

GAA ACT GGG AAG TTG GTC ATA TTG CCT CCC ACC AAG CAG CTG CTA CAT     4411
Glu Thr Gly Lys Leu Val Ile Leu Pro Pro Thr Lys Gln Leu Leu His
445                 450                 455                 460

TTT TGC CTG AAA GAC AGC AGC AGT CCT CCG GGG CCT GGG GAT CTG ACT     4459
Phe Cys Leu Lys Asp Ser Ser Ser Pro Pro Gly Pro Gly Asp Leu Thr
                465                 470                 475

GAG GAG AGG ACA GAG TTC CTG CGC AGC CAC AAC TCC CTG TCA TCT GGA AG  4509
Glu Glu Arg Thr Glu Phe Leu Arg Ser His Asn Ser Leu Ser Ser Gly Ser
            480                 485                 490
```

| | |
|---|---:|
| GTACACTCAC TGGGCCAGCC TTTTAGGACC TGAAAGCACA GCTCTGGAAA AGCAGCTCTC | 4569 |

```
CGTTCTGAGT CACCCCTACC CTCCTTAG C TCC CTG TCC GAT GAG GCT CCA GTC    4622
                                 Ser Leu Ser Asp Glu Ala Pro Val
                                                         495                 500

CTG CCC AAC ACC ACT CCA GAC CTC CTC CTT GTC ACC ACT GCC AAC CCA     4670
Leu Pro Asn Thr Thr Pro Asp Leu Leu Leu Val Thr Thr Ala Asn Pro
                505                 510                 515

TCT GCA CCT GGT ACT GAC AGA GAA ACA CCC CCT TCC CAG GTAAGCAGAA      4719
Ser Ala Pro Gly Thr Asp Arg Glu Thr Pro Pro Ser Gln
                520                 525                 530
```

| | |
|---|---:|
| ACAAACAGAG CTCTGGAGAT TCATTGCAGA GGTGACATTG GATGCTACAG CCTTGCTGTT | 4779 |

```
CACTTTTGTC CCCAG GAC CAG TCA GGA AGC CCC AGT AGC CAT GAA GAC ACC    4830
                Asp Gln Ser Gly Ser Pro Ser Ser His Glu Asp Thr
                                    535                 540

AGT GAC TCA GGC CCA GAA CTG AGG GCC TCC ATC CTG CCC AGA ACC TTG     4878
Ser Asp Ser Gly Pro Glu Leu Arg Ala Ser Ile Leu Pro Arg Thr Leu
545                 550                 555

TCT CTG CGG AAT TCC ATC AGT AAG A GTGAGTCTGG AGCCAGGGAA             4923
Ser Leu Arg Asn Ser Ile Ser Lys
    560                 565
```

| | |
|---|---:|
| TAGGGCAGGA GGAGAAGACA GCCCCTCCCC CCCATTCCAG CCCCTCCCTC CCCCAGCCC | 4983 |

```
CACCCTCCCT AAGCCTTCTC CTTTGACCTG CAG TT ATG TCG GAA GCT GGC AGT     5036
                                      Ile Met Ser Glu Ala Gly Ser
                                                              570

GAG ACC CTG GAG GAT GAG TGG CAG TCC ATC TCA GAG ATC GCC TCC ACT     5084
Glu Thr Leu Glu Asp Glu Trp Gln Ser Ile Ser Glu Ile Ala Ser Thr
575                 580                 585

TGC AAC ACA ATT CTG GAG TCA CTG TCC CGG GAG GTGAGGCCGC AAGGCCCAGA   5137
Cys Asn Thr Ile Leu Glu Ser Leu Ser Arg Glu
590                 595                 600
```

| | |
|---|---:|
| GGGAGGAGCC AGGAGGATGT TTATCCCTTC AGACCTGCCC ACAGTCTCTC TCTCTCCTAT | 5197 |

```
AG GGA CAA CCC ATC TCA GAG AGC GGA GAC CCC AAG GAA GCT TTA AAG      5244
   Gly Gln Pro Ile Ser Glu Ser Gly Asp Pro Lys Glu Ala Leu Lys
                    605                 610                 615

TGT GAT TCT GA   GTAAGTTTTC TGCCCTCACA TACCCACTCT TGTGTGTGTG        5295
Cys Asp Ser Glu
```

-continued

```
TCCTTCCCTG CCTGCCCATT GCAGTTGAAC ACTATCTAGG CTCTGCATCC ACAGATACCT    5355

AAGTCTCAGA AGACAGGGTT GGGTTCATTA TCAGTCAGGA GTGTCTGGGA GCCTGCACTG    5415

CTTCCGCTGA GTTCTGACCC CATGTCCTCA G G CCA GAA CCC GGG AGC CTG TCA    5468
                                      Pro Glu Pro Gly Ser Leu Ser
                                                             625
                                      620

GAA AAG GTC TCT CAC CTA GAG TCC ATG CTC TGG AAG CTC CAG GAG GAC    5516
Glu Lys Val Ser His Leu Glu Ser Met Leu Trp Lys Leu Gln Glu Asp
            630                  635                  640

CTG CAG AGG GTGAGGAGAG AGCCTGACGG GGGCGCACAG GGCTGCCCCT            5565
Leu Gln Arg
        645

GGCAAGGCTC TGACTACCAT TCTTCAACCT AG GAG AAG GCG GAC AGG GCA GCC    5618
                                     Glu Lys Ala Asp Arg Ala Ala
                                                     650

TTG GAG GAG GAG GTT CGG AGC CTC AGA CAC AAC AAC CAG AGG CTG CTG    5666
Leu Glu Glu Glu Val Arg Ser Leu Arg His Asn Asn Gln Arg Leu Leu
                655                  660                  665

GCA GAG TCC GAG AGT GCC GCC ACC CGC CTG CTC CTG GCC TCT AAG CAT    5714
Ala Glu Ser Glu Ser Ala Ala Thr Arg Leu Leu Leu Ala Ser Lys His
        670                  675                  680

CTG GGT GCA CCC ACT ACT GAC CTG GCC TGAGTTCCAA TCTGAATCTG          5761
Leu Gly Ala Pro Thr Thr Asp Leu Ala
685                  690

GACCTGCTTG GAACTGCCTG GCCCCTCAGA GCAACTGGGT CATACTAGTG CCCTTCCTCA    5821

GGACTTCTTC CCTGCGCTGA GGCGCGTCTT AGCACTGCCC CCTCTTCCCA GCCCATTTGG    5881

TGGCTAATGC CTGTCCCTGT TTGTAAATAT CCTGTAAAGA AAAGGAGACA TCAGAGTTTA    5941

AAAAAAAGAA ACAACAAGAA GAAGCAAACA ACTCTATTTG TGTTTGTGTG TCAAGATACA    6001

GAGGAGGGGG AGTCATCCCC TTTCCAAGGT CATATCAAGC TCCTAGGAGC AGTAGGACAG    6061

GTCCCAGGGG GGACATTGAC TTAGTGTTAA TCTGGCACCA AGCAGAGGCT CTGAGGATAG    6121

AACACCCCCT TGGCTCCCCT TCATTTATTG GGTTCTCTTG GAAAGCAGGT GGCCACGCTT    6181

CATGCCTGTC TGTTTGGAGC AGGAGAGGGA ACACTTCGAG CCTGCAGAGC GAACAACCAG    6241

GGGTGGGCTC TGGCCATGCA GTATGGAATT CCCGAATAGG CCCTGCTAAG CTGAGCTTCA    6301

GAGCATCATT GACTACCACT GGATGGATCA CCTGTTGCAG GCCCCAGCCA GTGCCTCATC    6361

AGCCTCTCCC CAGGGCTGCC TCTGCCTCGA GAAGCCCAGA CCCTGAGAGA GGACAGGATA    6421

AACATGGCTG AGTAACAGTG GGGCCATGAG CACAAGGAAG CCTTCTCTGA GGAGGCTAAT    6481

AAAAGGACTG AGTTTTGAAA GTTGAGTTCA CCAGCAGATG TCACAGGTAT CCAGGAGAAA    6541

CACTCTAGGA GCCACTGGGC CGAATTTGAG GTACCGAAGG AATCAGGGTT ACAGAGCCTT    6601

TAAGCTGGGT CAGAAAGGGT CATGCCAAGG TCCACTAGGG ATCC                    6645
```

( 2 ) INFORMATION FOR SEQ ID NO:5:

( i ) SEQUENCE CHARACTERISTICS:
        ( A ) LENGTH: 693 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Tyr Asn Asn Gln Glu Ala Gly Ala Ala Phe Met Gln Phe Leu Thr
 1               5                  10                  15

Leu Leu Gly Asp Val Val Arg Leu Lys Gly Phe Glu Ser Tyr Arg Ala
                20                  25                  30
```

-continued

```
Gln Leu Asp Thr Lys Thr Asp Ser Thr Gly Thr His Ser Leu Tyr Thr
             35                  40                  45
Thr Tyr Gln Asp His Glu Ile Met Phe His Val Ser Thr Met Leu Pro
         50                  55                  60
Tyr Thr Pro Asn Asn Gln Gln Leu Leu Arg Lys Arg His Ile Gly
 65                  70                  75                  80
Asn Asp Ile Val Thr Ile Val Phe Gln Glu Pro Gly Ser Lys Pro Phe
                 85                  90                  95
Cys Pro Thr Thr Ile Arg Ser His Phe Gln His Val Phe Leu Val Val
             100                 105                 110
Arg Ala His Ala Pro Cys Thr Pro His Thr Ser Tyr Arg Val Ala Val
             115                 120                 125
Ser Arg Thr Gln Asp Thr Pro Ala Phe Gly Pro Ala Leu Pro Glu Gly
         130                 135                 140
Gly Gly Pro Phe Ala Ala Asn Ala Asp Phe Arg Ala Phe Leu Leu Ala
145                 150                 155                 160
Lys Ala Leu Asn Gly Glu Gln Ala Ala Gly His Ala Arg Gln Phe His
                 165                 170                 175
Ala Met Ala Thr Arg Thr Arg Gln Gln Tyr Leu Gln Asp Leu Ala Thr
             180                 185                 190
Asn Glu Val Thr Thr Thr Ser Leu Asp Ser Ala Ser Arg Phe Gly Leu
             195                 200                 205
Pro Ser Leu Gly Gly Arg Arg Ala Thr Pro Arg Ser Pro Gly Ala
     210                 215                 220
Asp Val Gln Ala Ala Gly Ala Leu Met Trp Gly Val Arg Ala Ala Pro
225                 230                 235                 240
Gly Ala Arg Val Ala Ala Gly Ala Glu Thr Ser Gly Pro Asp Asp Ala
                 245                 250                 255
Glu Val Pro Cys Leu Leu Gly Ile Ser Ala Glu Thr Leu Val Leu Val
             260                 265                 270
Ala Pro Arg Asp Gly Arg Val Val Phe Asn Cys Ala Cys Arg Asp Val
         275                 280                 285
Leu Ala Trp Thr Phe Ser Glu His Gln Leu Asp Leu Tyr His Gly Arg
     290                 295                 300
Gly Glu Ala Ile Thr Leu Arg Leu Asp Gly Ala Pro Gly Gln Ala Val
305                 310                 315                 320
Gly Glu Val Val Ala Arg Leu Gln Leu Val Ser Arg Gly Cys Glu Thr
                 325                 330                 335
Arg Glu Leu Ala Leu Pro Arg Asp Gly Gln Gly Arg Leu Gly Phe Glu
             340                 345                 350
Val Asp Ala Glu Gly Phe Ile Thr His Val Glu Arg Phe Thr Phe Ala
         355                 360                 365
Glu Thr Thr Gly Leu Arg Pro Gly Ala Arg Leu Leu Arg Val Cys Gly
     370                 375                 380
Gln Thr Leu Pro Lys Leu Gly Pro Glu Ala Ala Ala Gln Met Leu Arg
385                 390                 395                 400
Ser Ala Pro Lys Val Cys Val Thr Val Leu Pro Pro Asp Glu Ser Gly
                 405                 410                 415
Arg Pro Gln Arg Ser Phe Ser Glu Leu Tyr Met Leu Ser Leu Lys Glu
             420                 425                 430
Pro Ser Arg Arg Gly Gly Pro Glu Pro Val Gln Asp Glu Thr Gly Lys
             435                 440                 445
```

-continued

| | | | | | | | | | | | | | |
|---|---|---|---|---|---|---|---|---|---|---|---|---|---|
| Leu | Val | Ile | Leu | Pro | Pro | Thr | Lys | Gln | Leu | Leu | His | Phe | Cys | Leu | Lys |
| 450 | | | | | 455 | | | | | 460 | | | | | |
| Asp | Ser | Ser | Ser | Pro | Pro | Gly | Pro | Gly | Asp | Leu | Thr | Glu | Glu | Arg | Thr |
| 465 | | | | | 470 | | | | | 475 | | | | | 480 |
| Glu | Phe | Leu | Arg | Ser | His | Asn | Ser | Leu | Ser | Gly | Ser | Ser | Leu | Ser |
| | | | | 485 | | | | | 490 | | | | | 495 |
| Asp | Glu | Ala | Pro | Val | Leu | Pro | Asn | Thr | Thr | Pro | Asp | Leu | Leu | Leu | Val |
| | | | 500 | | | | | 505 | | | | | 510 | | |
| Thr | Thr | Ala | Asn | Pro | Ser | Ala | Pro | Gly | Thr | Asp | Arg | Glu | Thr | Pro | Pro |
| | | | 515 | | | | | 520 | | | | | 525 | | |
| Ser | Gln | Asp | Gln | Ser | Gly | Ser | Pro | Ser | Ser | His | Glu | Asp | Thr | Ser | Asp |
| | 530 | | | | | 535 | | | | | 540 | | | | |
| Ser | Gly | Pro | Glu | Leu | Arg | Ala | Ser | Ile | Leu | Pro | Arg | Thr | Leu | Ser | Leu |
| 545 | | | | | 550 | | | | | 555 | | | | | 560 |
| Arg | Asn | Ser | Ile | Ser | Lys | Ile | Met | Ser | Glu | Ala | Gly | Ser | Glu | Thr | Leu |
| | | | | 565 | | | | | 570 | | | | | 575 | |
| Glu | Asp | Glu | Trp | Gln | Ser | Ile | Ser | Glu | Ile | Ala | Ser | Thr | Cys | Asn | Thr |
| | | | 580 | | | | | 585 | | | | | 590 | | |
| Ile | Leu | Glu | Ser | Leu | Ser | Arg | Glu | Gly | Gln | Pro | Ile | Ser | Glu | Ser | Gly |
| | | | 595 | | | | | 600 | | | | | 605 | | |
| Asp | Pro | Lys | Glu | Ala | Leu | Lys | Cys | Asp | Ser | Glu | Pro | Glu | Pro | Gly | Ser |
| 610 | | | | | 615 | | | | | 620 | | | | | |
| Leu | Ser | Glu | Lys | Val | Ser | His | Leu | Glu | Ser | Met | Leu | Trp | Lys | Leu | Gln |
| 625 | | | | | 630 | | | | | 635 | | | | | 640 |
| Glu | Asp | Leu | Gln | Arg | Glu | Lys | Ala | Asp | Arg | Ala | Ala | Leu | Glu | Glu | Glu |
| | | | | 645 | | | | | 650 | | | | | 655 | |
| Val | Arg | Ser | Leu | Arg | His | Asn | Asn | Gln | Arg | Leu | Leu | Ala | Glu | Ser | Glu |
| | | | | 660 | | | | | 665 | | | | | 670 | |
| Ser | Ala | Ala | Thr | Arg | Leu | Leu | Leu | Ala | Ser | Lys | His | Leu | Gly | Ala | Pro |
| | | | 675 | | | | | 680 | | | | | 685 | | |
| Thr | Thr | Asp | Leu | Ala |
| | | | | 690 |

( 2 ) INFORMATION FOR SEQ ID NO:6:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

| | | | | | | | | | | | | | |
|---|---|---|---|---|---|---|---|---|---|---|---|---|---|
| Gly | Gln | Gly | Ser | Arg | Arg | Arg | Asn | Tyr | Asn | Asn | Gln | Glu | Ala | Gly | Ala |
| 1 | | | | 5 | | | | | 10 | | | | | 15 | |
| Ala | Phe | Met | Gln | Phe | Leu | Thr | Leu | Leu | Gly | Asp | Val | Val | Arg | Leu | Lys |
| | | | 20 | | | | | 25 | | | | | 30 | | |
| Gly | Phe | Glu | Ser | Tyr | Arg | Ala | Gln | Leu | Asp | Thr | Lys | Thr | Asp | Ser | Thr |
| | | | 35 | | | | | 40 | | | | | 45 | | |
| Gly | Thr | His | Ser | Leu | Tyr | Thr | Thr | Tyr | Gln | Asp | His | Glu | Ile | Met | Phe |
| | | 50 | | | | | 55 | | | | | 60 | | | |
| His | Val | Ser | Thr | Met | Leu | Pro | Tyr | Thr | Pro | Asn | Asn | Gln | Gln | Gln | Leu |
| 65 | | | | | 70 | | | | | 75 | | | | | 80 |
| Leu | Arg | Lys | Arg | His | Ile | Gly | Asn | Asp | Ile | Val | Thr | Ile | Val | Phe | Gln |
| | | | | 85 | | | | | 90 | | | | | 95 | |
| Glu | Pro | Gly | Ser | Lys | Pro | Phe | Cys | Pro | Thr | Thr | Ile | Arg | Ser | His | Phe |
| | | | | 100 | | | | | 105 | | | | | 110 | |

```
Gln  His  Val  Phe  Leu  Val  Val  Arg  Ala  His  Ala  Pro  Cys  Thr  Pro  His
     115                      120                      125

Thr  Ser  Tyr  Arg  Val  Ala  Val  Ser  Arg  Thr  Gln  Asp  Thr  Pro  Ala  Phe
     130                      135                 140

Gly  Pro  Ala  Leu  Pro  Glu  Gly  Gly  Pro  Ala  Ala  Asn  Ala  Asp
145                      150                 155                           160

Phe  Arg  Ala  Phe  Leu  Leu  Ala  Lys  Ala  Leu  Asn  Gly  Glu  Gln  Ala  Ala
               165                      170                           175

Gly  His  Ala  Arg  Gln  Phe  His  Ala  Met  Ala  Thr  Arg  Thr  Arg  Gln  Gln
          180                      185                           190

Tyr  Leu  Gln  Asp  Leu  Ala  Thr  Asn  Glu  Val  Thr  Thr  Thr  Ser  Leu  Asp
          195                      200                      205

Ser  Ala  Ser  Arg  Phe  Gly  Leu  Pro  Ser  Leu  Gly  Gly  Arg  Arg  Arg  Ala
     210                      215                      220

Thr  Pro  Arg  Ser  Pro  Gly  Ala  Asp  Val  Gln  Ala  Ala  Gly  Ala  Leu  Met
225                      230                      235                           240
```

(2) INFORMATION FOR SEQ ID NO:7:

(i) SEQUENCE CHARACTERISTICS:
        (A) LENGTH: 238 amino acids
        (B) TYPE: amino acid
        (C) STRANDEDNESS: single
        (D) TOPOLOGY: linear (xi) SEQUENCE DESCRIPTION: SEQ ID NO:7:

```
Gly  Gln  Thr  Ser  Glu  Glu  Glu  Leu  Phe  Ser  Thr  Asn  Glu  Glu  Ser  Pro
1                   5                        10                       15

Ala  Phe  Val  Glu  Phe  Leu  Glu  Phe  Leu  Gly  Gln  Lys  Val  Lys  Leu  Gln
               20                      25                      30

Asp  Phe  Xaa  Gly  Phe  Arg  Gly  Gly  Leu  Asp  Val  Thr  His  Gly  Gln  Thr
          35                      40                      45

Gly  Thr  Glu  Ser  Val  Tyr  Cys  Asn  Phe  Arg  Asn  Lys  Glu  Ile  Met  Phe
     50                      55                      60

His  Val  Ser  Thr  Lys  Leu  Pro  Tyr  Thr  Glu  Gly  Asp  Ala  Gln  Gln  Leu
65                       70                      75                            80

Gln  Arg  Lys  Arg  His  Ile  Gly  Asn  Asp  Ile  Val  Ala  Val  Val  Phe  Gln
               85                      90                      95

Asp  Glu  Asn  Thr  Pro  Phe  Val  Pro  Asp  Met  Ile  Ala  Ser  Asn  Phe  Leu
          100                     105                     110

His  Ala  Tyr  Val  Val  Val  Gln  Ala  Glu  Gly  Gly  Gly  Pro  Asp  Gly  Pro
          115                     120                     125

Leu  Tyr  Lys  Val  Ser  Val  Thr  Ala  Arg  Asp  Asp  Val  Pro  Phe  Phe  Gly
     130                     135                     140

Pro  Pro  Leu  Pro  Asp  Pro  Ala  Val  Phe  Arg  Lys  Gly  Pro  Glu  Phe  Gln
145                     150                     155                           160

Glu  Phe  Leu  Leu  Thr  Lys  Leu  Ile  Asn  Ala  Glu  Tyr  Ala  Cys  Tyr  Lys
               165                     170                     175

Ala  Glu  Lys  Phe  Ala  Lys  Leu  Glu  Glu  Arg  Thr  Arg  Ala  Ala  Leu  Leu
          180                     185                     190

Glu  Thr  Leu  Tyr  Glu  Glu  Leu  His  Ile  His  Ser  Gln  Ser  Met  Met  Gly
          195                     200                     205

Leu  Gly  Gly  Asp  Glu  Asp  Lys  Met  Glu  Asn  Gly  Ser  Gly  Gly  Gly  Gly
     210                     215                     220

Phe  Phe  Glu  Ser  Phe  Lys  Arg  Val  Ile  Arg  Ser  Arg  Ser  Gln
225                     230                     235
```